(12) United States Patent
Salituro et al.

(10) Patent No.: US 12,060,386 B2
(45) Date of Patent: Aug. 13, 2024

(54) COMPOSITIONS AND METHODS FOR TREATING CNS DISORDERS

(71) Applicant: Sage Therapeutics, Inc., Cambridge, MA (US)

(72) Inventors: Francesco G. Salituro, Marlborough, MA (US); Albert Jean Robichaud, Boston, MA (US)

(73) Assignee: Sage Therapeutics, Inc., Cambridge, MA (US)

( * ) Notice: Subject to any disclaimer, the term of this patent is extended or adjusted under 35 U.S.C. 154(b) by 0 days.

(21) Appl. No.: 18/305,529

(22) Filed: Apr. 24, 2023

(65) Prior Publication Data

US 2024/0092824 A1    Mar. 21, 2024

Related U.S. Application Data

(63) Continuation of application No. 17/545,290, filed on Dec. 8, 2021, now Pat. No. 11,667,668, which is a continuation of application No. 16/770,398, filed as application No. PCT/US2018/064546 on Dec. 7, 2018, now abandoned.

(60) Provisional application No. 62/731,539, filed on Sep. 14, 2018, provisional application No. 62/596,725, filed on Dec. 8, 2017.

(51) Int. Cl.
   *A61P 25/24* (2006.01)
   *C07J 43/00* (2006.01)

(52) U.S. Cl.
   CPC ............. *C07J 43/003* (2013.01); *A61P 25/24* (2018.01); *C07B 2200/05* (2013.01)

(58) Field of Classification Search
   CPC ...... C07J 43/003; C07B 2200/05; A61P 25/24
   See application file for complete search history.

(56) References Cited

U.S. PATENT DOCUMENTS

| | | | |
|---|---|---|---|
| 9,365,611 B2 | 6/2016 | Martinez Botella et al. | |
| 9,512,165 B2 * | 12/2016 | Martinez Botella | A61P 25/14 |
| 9,630,986 B2 | 4/2017 | Covey et al. | |
| 9,676,812 B2 | 6/2017 | Covey | |
| 9,725,481 B2 | 8/2017 | Martinez Botella et al. | |
| 10,023,606 B2 | 7/2018 | Martinez Botella et al. | |
| 10,172,871 B2 | 1/2019 | Martinez Botella et al. | |
| 10,246,482 B2 | 4/2019 | Harrison et al. | |
| 10,251,894 B2 | 4/2019 | Rogawski et al. | |
| 10,322,139 B2 | 6/2019 | Reddy | |
| 10,323,059 B2 | 6/2019 | Martinez Botella et al. | |
| 10,329,320 B2 | 6/2019 | Robichaud et al. | |
| 10,342,809 B2 | 7/2019 | Covey et al. | |
| 10,342,810 B2 | 7/2019 | Martinez Botella et al. | |
| 10,377,790 B2 | 8/2019 | Martinez Botella | |
| 10,391,106 B2 | 8/2019 | Martinez Botella | |
| 10,426,786 B2 | 10/2019 | Rogawski et al. | |
| 10,426,837 B2 | 10/2019 | Robichaud et al. | |
| 10,435,431 B2 | 10/2019 | Upasani et al. | |
| 10,577,390 B2 | 3/2020 | Martinez Botella et al. | |
| 10,745,436 B2 | 8/2020 | Harrison et al. | |
| 10,774,108 B2 | 9/2020 | Martinez Botella et al. | |
| 10,822,370 B2 | 11/2020 | Martinez Botella et al. | |
| 10,870,677 B2 * | 12/2020 | Martinez Botella | C07D 249/04 |
| 10,940,156 B2 | 3/2021 | Kanes et al. | |
| 11,046,728 B2 | 6/2021 | Martinez Botella et al. | |
| 11,124,538 B2 | 9/2021 | Robichaud et al. | |
| 11,147,877 B2 | 10/2021 | Robichaud et al. | |
| 11,149,057 B2 | 10/2021 | Harrison et al. | |
| 11,236,121 B2 | 2/2022 | Watson et al. | |
| 11,241,446 B2 | 2/2022 | Martinez Botella et al. | |

(Continued)

FOREIGN PATENT DOCUMENTS

| | | |
|---|---|---|
| EP | 3260463 A1 | 12/2017 |
| WO | 1995026325 A2 | 10/1995 |

(Continued)

OTHER PUBLICATIONS

Foster, Deuterium isotope effects in studies of drug metabolism. Trends in Pharmacological Sciences, vol. 5, pp. 524-527 (Abstact) (Year: 1984).

(Continued)

*Primary Examiner* — Timothy R Rozof
(74) *Attorney, Agent, or Firm* — Honigman LLP; Kathryn D. Doyle; Jonathan P. O'Brien

(57) ABSTRACT

Provided herein is a compound of Formula (I)

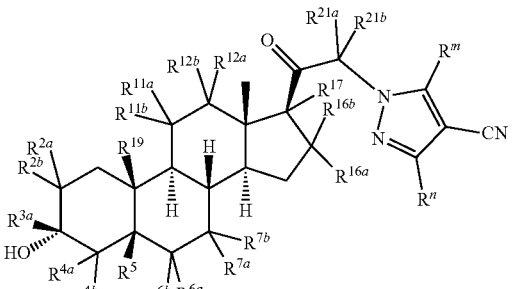

or a pharmaceutically acceptable salt thereof, wherein $R^{3a}$, $R^5$, $R^{6a}$, $R^{6b}$, $R^{17}$, $R^{21a}$, $R^{21b}$, $R^m$, $R^n$, $R^{16a}$, $R^{16b}$, $R^{7a}$, $R^{7b}$, $R^{12a}$, $R^{12b}$, $R^{11a}$, $R^{11b}$, $R^{2a}$, $R^{2b}$, $R^{19}$, $R^{4a}$, and $R^{4b}$ are defined herein. Also provided herein are pharmaceutical compositions comprising a compound of Formula (I) and methods of using the compounds, e.g., in the treatment of CNS-related disorders.

10 Claims, No Drawings

(56) References Cited

U.S. PATENT DOCUMENTS

| | | |
|---|---|---|
| 11,261,211 B2 | 3/2022 | Martinez Botella et al. |
| 11,344,563 B2 | 5/2022 | Martinez Botella et al. |
| 11,396,525 B2 | 7/2022 | Robichaud et al. |
| 11,426,417 B2 | 8/2022 | Reddy |
| 11,498,940 B2 | 11/2022 | Martinez Botella et al. |
| 11,510,929 B2 | 11/2022 | Rogawski et al. |
| 11,530,237 B2 | 12/2022 | Martinez Botella et al. |
| 11,542,297 B2 | 1/2023 | Martinez Botella et al. |
| 11,554,125 B2 | 1/2023 | Kanes et al. |
| 11,634,453 B2 | 4/2023 | Blanco-Pillado et al. |
| 2014/0050789 A1 | 2/2014 | Rogawski et al. |
| 2014/0057885 A1 | 2/2014 | Reddy et al. |
| 2014/0235600 A1 | 8/2014 | Covey et al. |
| 2015/0018327 A1 | 1/2015 | Reddy |
| 2015/0175651 A1 | 6/2015 | Salituro et al. |
| 2015/0291654 A1 | 10/2015 | Upasani et al. |
| 2015/0313915 A1 | 11/2015 | Rogawski et al. |
| 2015/0315230 A1 | 11/2015 | Covey et al. |
| 2016/0068563 A1 | 3/2016 | Martinez Botella et al. |
| 2016/0083417 A1 | 3/2016 | Martinez Botella et al. |
| 2016/0083418 A1 | 3/2016 | Martinez Botella et al. |
| 2016/0108080 A1 | 4/2016 | Martinez Botella et al. |
| 2016/0152658 A1 | 6/2016 | Martinez Botella et al. |
| 2016/0229887 A1 | 8/2016 | Martinez Botella et al. |
| 2017/0190732 A1 | 7/2017 | Covey et al. |
| 2017/0232006 A1 | 8/2017 | Covey et al. |
| 2017/0233432 A1 | 8/2017 | Martinez Botella et al. |
| 2017/0233433 A1 | 8/2017 | Martinez Botella et al. |
| 2017/0240589 A1 | 8/2017 | Martinez Botella et al. |
| 2017/0246191 A1 | 8/2017 | Martinez Botella et al. |
| 2017/0247406 A1 | 8/2017 | Harrison et al. |
| 2017/0319695 A1 | 11/2017 | Robichaud et al. |
| 2017/0342102 A1 | 11/2017 | Martinez Botella et al. |
| 2017/0342103 A1 | 11/2017 | Upasani et al. |
| 2017/0348326 A1 | 12/2017 | Reddy |
| 2017/0348327 A1 | 12/2017 | Kanes et al. |
| 2018/0030083 A1 | 2/2018 | Lv et al. |
| 2018/0037602 A1 | 2/2018 | Robichaud et al. |
| 2018/0051052 A1 | 2/2018 | Martinez Botella et al. |
| 2018/0133229 A1 | 5/2018 | Rogawski et al. |
| 2018/0141971 A1 | 5/2018 | Martinez Botella et al. |
| 2018/0153906 A1 | 6/2018 | Rogawski et al. |
| 2018/0179247 A1 | 6/2018 | Botella et al. |
| 2018/0193357 A1 | 7/2018 | Rogawski et al. |
| 2018/0215779 A1 | 8/2018 | Martinez Botella et al. |
| 2018/0311258 A1 | 11/2018 | Robichaud et al. |
| 2018/0311262 A1 | 11/2018 | Martinez Botella et al. |
| 2019/0008873 A1 | 1/2019 | Salituro et al. |
| 2019/0038639 A1 | 2/2019 | Reddy et al. |
| 2019/0112331 A1 | 4/2019 | Botella et al. |
| 2019/0142845 A1 | 5/2019 | Rogawski et al. |
| 2019/0169226 A1 | 6/2019 | Harrison et al. |
| 2019/0177358 A1 | 6/2019 | Martinez Botella et al. |
| 2019/0177359 A1 | 6/2019 | Watson et al. |
| 2019/0233465 A1 | 8/2019 | Robichaud et al. |
| 2019/0247402 A1 | 8/2019 | Reddy |
| 2019/0248831 A1 | 8/2019 | Robichaud et al. |
| 2019/0269699 A1 | 9/2019 | Reddy |
| 2019/0350944 A1 | 11/2019 | Salituro et al. |
| 2020/0016178 A1 | 1/2020 | Martinez Botella et al. |
| 2020/0017542 A1 | 1/2020 | Martinez Botella et al. |
| 2020/0024301 A1 | 1/2020 | Martinez Botella et al. |
| 2020/0024302 A1 | 1/2020 | Martinez Botella et al. |
| 2020/0048300 A1 | 2/2020 | Martinez Botella et al. |
| 2020/0113916 A1 | 4/2020 | Covey et al. |
| 2020/0113917 A1 | 4/2020 | Kanes et al. |
| 2020/0155576 A1 | 5/2020 | Martinez Botella et al. |
| 2020/0171049 A1 | 6/2020 | Kanes et al. |
| 2020/0215078 A1 | 7/2020 | Rogawski et al. |
| 2020/0223884 A1 | 7/2020 | Upasani et al. |
| 2020/0246459 A1 | 8/2020 | Robichaud et al. |
| 2020/0253985 A1 | 8/2020 | Kanes et al. |
| 2020/0276209 A1 | 9/2020 | Colquhoun et al. |
| 2020/0281943 A1 | 9/2020 | Hoffmann et al. |
| 2020/0306262 A1 | 10/2020 | Doherty |
| 2020/0306265 A1 | 10/2020 | Kanes et al. |
| 2020/0354399 A1 | 11/2020 | Robichaud et al. |
| 2020/0377547 A1 | 12/2020 | Salituro et al. |
| 2020/0392177 A1 | 12/2020 | Martinez Botella et al. |
| 2021/0017218 A1 | 1/2021 | Martinez Botella et al. |
| 2021/0040141 A1 | 2/2021 | Upasani et al. |
| 2021/0061848 A1 | 3/2021 | Martinez Botella et al. |
| 2021/0061850 A1 | 3/2021 | Martinez Botella et al. |
| 2021/0087223 A1 | 3/2021 | Martinez Botella et al. |
| 2021/0094981 A1 | 4/2021 | Harrison et al. |
| 2021/0100817 A1 | 4/2021 | Rogawski et al. |
| 2021/0101928 A1 | 4/2021 | Robichaud et al. |
| 2021/0113590 A1 | 4/2021 | Robichaud et al. |
| 2021/0139531 A1 | 5/2021 | Botella et al. |
| 2021/0308149 A1 | 10/2021 | Covey et al. |
| 2021/0338692 A1 | 11/2021 | Kanes et al. |
| 2021/0340172 A1 | 11/2021 | Blanco-Pillado et al. |
| 2021/0347812 A1 | 11/2021 | Robichaud et al. |
| 2021/0363175 A1 | 11/2021 | Salituro et al. |
| 2021/0369734 A1 | 12/2021 | Doherty |
| 2021/0403502 A1 | 12/2021 | Harrison et al. |
| 2022/0023313 A1 | 1/2022 | Kanes et al. |
| 2022/0098231 A1 | 3/2022 | Salituro et al. |
| 2022/0110949 A1 | 4/2022 | Doherty et al. |
| 2022/0110950 A1 | 4/2022 | Martinez Botella et al. |
| 2022/0152050 A1 | 5/2022 | Reddy et al. |
| 2022/0169674 A1 | 6/2022 | Watson et al. |
| 2022/0213137 A1 | 7/2022 | Martinez Botella et al. |
| 2022/0220150 A1 | 7/2022 | Martinez Botella et al. |
| 2022/0315621 A1 | 10/2022 | Robichaud et al. |
| 2022/0323462 A1 | 10/2022 | Kanes et al. |
| 2022/0372067 A1 | 11/2022 | Blanco-Pillado et al. |
| 2022/0380405 A1 | 12/2022 | Salituro et al. |
| 2023/0018765 A1 | 1/2023 | Kanes et al. |
| 2023/0021308 A9 | 1/2023 | Robichaud et al. |
| 2023/0046825 A1 | 2/2023 | Blanco-Pillado et al. |
| 2023/0057130 A1 | 2/2023 | Watson et al. |
| 2023/0085354 A1 | 3/2023 | Robichaud et al. |
| 2023/0113666 A1 | 4/2023 | Martinez Botella et al. |
| 2023/0116347 A1 | 4/2023 | Robichaud et al. |

FOREIGN PATENT DOCUMENTS

| | | |
|---|---|---|
| WO | 2010054158 A2 | 5/2010 |
| WO | 2013056181 A1 | 4/2013 |
| WO | 2013112605 A2 | 8/2013 |
| WO | 2013188792 A2 | 12/2013 |
| WO | 2013192097 A1 | 12/2013 |
| WO | 2014028398 A2 | 2/2014 |
| WO | 2014031792 A2 | 2/2014 |
| WO | 2014085668 A1 | 6/2014 |
| WO | 2014100228 A1 | 6/2014 |
| WO | 2014122480 A1 | 8/2014 |
| WO | 2014169831 A1 | 10/2014 |
| WO | 2014169832 A1 | 10/2014 |
| WO | 2014169833 A1 | 10/2014 |
| WO | 2014169836 A1 | 10/2014 |
| WO | 2015010054 A2 | 1/2015 |
| WO | 2015027227 A1 | 2/2015 |
| WO | 2015180679 A1 | 12/2015 |
| WO | 2015195962 A1 | 12/2015 |
| WO | 2016040322 A1 | 3/2016 |
| WO | 2016061527 A1 | 4/2016 |
| WO | 2016061537 A1 | 4/2016 |
| WO | 2016082789 A1 | 6/2016 |
| WO | 2016123056 A1 | 8/2016 |
| WO | 2016131414 A1 | 8/2016 |
| WO | 2016134301 A1 | 8/2016 |
| WO | 2016164763 A1 | 10/2016 |
| WO | 2016205721 A1 | 12/2016 |
| WO | 2017087864 A1 | 5/2017 |
| WO | 2017156103 A1 | 9/2017 |
| WO | 2018013613 A1 | 1/2018 |
| WO | 2018013615 A1 | 1/2018 |
| WO | 2018039378 A1 | 3/2018 |
| WO | 2019051264 A1 | 3/2019 |
| WO | 2019051477 A1 | 3/2019 |
| WO | 2019055764 A1 | 3/2019 |

(56) References Cited

FOREIGN PATENT DOCUMENTS

| WO | 2019113494 A1 | 6/2019 |
| WO | 2019126741 A1 | 6/2019 |
| WO | 2019126761 A1 | 6/2019 |
| WO | 2019140272 A1 | 7/2019 |
| WO | 2019241442 A1 | 12/2019 |
| WO | 2020077255 A1 | 4/2020 |
| WO | 2020082065 A1 | 4/2020 |
| WO | 2020118060 A1 | 6/2020 |
| WO | 2020132504 A1 | 6/2020 |
| WO | 2020243027 A1 | 12/2020 |
| WO | 2020243488 A1 | 12/2020 |
| WO | 2020264495 A1 | 12/2020 |
| WO | 2020264509 A1 | 12/2020 |
| WO | 2020264512 A1 | 12/2020 |
| WO | 2021113786 A1 | 6/2021 |
| WO | 2021168106 A1 | 8/2021 |
| WO | 2021188778 A2 | 9/2021 |
| WO | 2021195297 A1 | 9/2021 |
| WO | 2021195301 A1 | 9/2021 |
| WO | 2021262836 A1 | 12/2021 |
| WO | 2022020363 A1 | 1/2022 |
| WO | 2022040545 A1 | 2/2022 |
| WO | 2022020363 A9 | 3/2022 |
| WO | 2022115381 A1 | 6/2022 |
| WO | 2022165017 A1 | 8/2022 |
| WO | 2022177718 A1 | 8/2022 |
| WO | 2022197901 A1 | 9/2022 |
| WO | 2022221195 A1 | 10/2022 |
| WO | 2022232494 A1 | 11/2022 |
| WO | 2022232504 A1 | 11/2022 |
| WO | 2023158668 A1 | 8/2023 |
| WO | 2023163879 A1 | 8/2023 |

OTHER PUBLICATIONS

Johnson et al. "Deuterium Labelled Steroid Hormones: Syntheses and Applications in Quantitation and Endocrinology", Journal of Steroid Biochemistry, vol. 14, 1981, pp. 793-800.

Kushner et al., Pharmacological uses and perspectives of heavy water and deuterated compounds. Canadian J. Physiology and Pharmacology, vol. 77, pp. 79-88 (Year: 1999).

Adams, et al., "The estrogenic activity and enzymic oxidation of 17b-estradiol-17a-d1", Steroids, Elsevier Science Publishers, (1965), pp. 75-84.

Blake, M.I., et al., "Studies with Deuterated Drugs", J. Pharm. Sci., 1975, vol. 64, pp. 367-391.

Buteau, K.C., "Deuterated Drugs: Unexpectedly Nonobvious?", J. High Technology Law, 2009, vol. X, pp. 22-74.

Dyck et al., Effects of Deuterium Substitution on the Catabolism of beta-Phenylethylamine: An In Vivo Study. J. Nerochem., vol. 46 (2), pp. 399-404 (Year: 1986).

International Search Report and Written Opinion for Corresponding International Application No. PCT/US2018/064546 dated Apr. 9, 2019.

Sanderson, K., "Big interest in heavy drugs", Nature, 2009, vol. 458, pp. 269.

* cited by examiner

COMPOSITIONS AND METHODS FOR TREATING CNS DISORDERS

CROSS-REFERENCE TO RELATED APPLICATIONS

The present application is a continuation of U.S. application Ser. No. 17/545,290, filed Dec. 8, 2021, which is a continuation of U.S. application Ser. No. 16/770,398, filed Jun. 5, 2020, which is a U.S. National Phase Application under 35 U.S.C. § 371 of International Application PCT/US2018/064546, filed Dec. 7, 2018, which claims priority to U.S. Ser. No. 62/596,725 filed Dec. 8, 2017 and U.S. Ser. No. 62/731,539 filed Sep. 14, 2018, the contents of each of which are incorporated herein by reference in their entirety.

BACKGROUND OF THE INVENTION

Brain excitability is defined as the level of arousal of an animal, a continuum that ranges from coma to convulsions, and is regulated by various neurotransmitters. In general, neurotransmitters are responsible for regulating the conductance of ions across neuronal membranes. At rest, the neuronal membrane possesses a potential (or membrane voltage) of approximately —70 mV, the cell interior being negative with respect to the cell exterior. The potential (voltage) is the result of ion (K+, Na+, Cl−, organic anions) balance across the neuronal semipermeable membrane. Neurotransmitters are stored in presynaptic vesicles and are released under the influence of neuronal action potentials. When released into the synaptic cleft, an excitatory chemical transmitter such as acetylcholine will cause membrane depolarization (change of potential from −70 mV to −50 mV). This effect is mediated by postsynaptic nicotinic receptors which are stimulated by acetylcholine to increase membrane permeability to Na+ ions. The reduced membrane potential stimulates neuronal excitability in the form of a postsynaptic action potential.

In the case of the GABA receptor complex (GRC), the effect on brain excitability is mediated by γ-aminobutyric acid (GABA), a neurotransmitter. GABA has a profound influence on overall brain excitability because up to 40% of the neurons in the brain utilize GABA as a neurotransmitter. GABA regulates the excitability of individual neurons by regulating the conductance of chloride ions across the neuronal membrane. GABA interacts with its recognition site on the GRC to facilitate the flow of chloride ions down an electrochemical gradient of the GRC into the cell. An intracellular increase in the levels of this anion causes hyperpolarization of the transmembrane potential, rendering the neuron less susceptible to excitatory inputs, i.e., reduced neuron excitability. In other words, the higher the chloride ion concentration in the neuron, the lower the brain excitability and level of arousal.

It is well-documented that the GRC is responsible for the mediation of anxiety, seizure activity, and sedation. Thus, GABA and drugs that act like GABA or facilitate the effects of GABA (e.g., the therapeutically useful barbiturates and benzodiazepines (BZs), such as Valium®) produce their therapeutically useful effects by interacting with specific regulatory sites on the GRC. Accumulated evidence has now indicated that in addition to the benzodiazepine and barbiturate binding site, the GRC contains a distinct site for neuroactive steroids. See, e.g., Lan, N. C. et al., Neurochem. Res. (1991) 16:347-356.

Neuroactive steroids can occur endogenously. The most potent endogenous neuroactive steroids are 3α-hydroxy-5-reduced pregnan-20-one and 3α-21-dihydroxy-5-reduced pregnan-20-one, metabolites of hormonal steroids progesterone and deoxycorticosterone, respectively. The ability of these steroid metabolites to alter brain excitability was recognized in 1986 (Majewska, M. D. et al., Science 232: 1004-1007 (1986); Harrison, N. L. et al., J Pharmacol. Exp. Ther. 241:346-353 (1987)).

New and improved compounds are needed that act as modulating agents for brain excitability, as well as agents for the prevention and treatment of CNS-related diseases. The compounds, compositions, and methods described herein are directed toward this end.

SUMMARY OF THE INVENTION

Provided herein are neuroactive steroids designed, for example, to act as GABA modulators. The compounds of the Formula (I) are compounds that comprise deuterium levels that are above the naturally-occurring levels. In some embodiments, such compounds are envisioned to be useful as therapeutic agents for treating a CNS-related disorder.

In one aspect, provided herein is a compound of Formula (I)

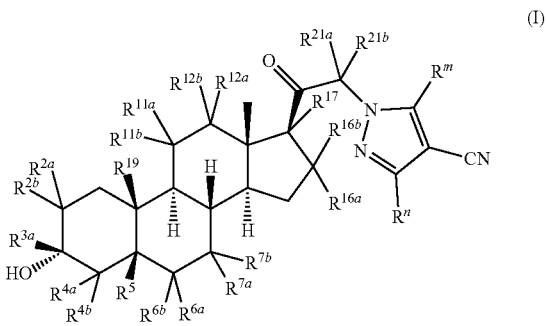

or a pharmaceutically acceptable salt thereof, wherein $R^{3a}$ is $C_1$-$C_6$ alkyl optionally substituted with 1 or more independent occurrences of deuterium or $X^2$—$OX^3$, wherein each of $X^2$ and $X^3$ is independently a $C_1$-$C_6$ alkylene optionally substituted with 1 more occurrences of deuterium; and each of $R^5$, $R^{6a}$, $R^{6b}$, $R^{17}$, $R^{21a}$, $R^{21b}$, $R^m$, $R^n$, $R^{16a}$, $R^{16b}$, $R^{7a}$, $R^{7b}$, $R^{12a}$, $R^{12b}$, $R^{11a}$, $R^{11b}$, $R^{2a}$, $R^{2b}$, $R^{19}$, $R^{4a}$, and $R^{4b}$ is independently selected from the group consisting of hydrogen and deuterium, provided that (a) if $R^{3a}$ is $C_1$-$C_6$ alkyl with no occurrences of deuterium or $X^2$—$OX^3$, wherein each of $X^2$ and $X^3$ is independently an $C_1$-$C_6$ alkylene with no occurrences of deuterium, then at least one of $R^5$, $R^{6a}$, $R^{6b}$, $R^{17}$, $R^{21a}$, $R^{21b}$, $R^m$, and $R^n$, $R^{16a}$, $R^{16b}$, $R^{7a}$, $R^{7b}$, $R^{12a}$, $R^{12b}$, $R^{11a}$, $R^{11b}$, $R^{2a}$, $R^{2b}$, $R^{19}$, $R^{4a}$, and $R^{4b}$ is deuterium, or (b) if all of $R^5$, $R^{6a}$, $R^{6b}$, $R^{17}$, $R^{21a}$, $R^{21b}$, $R^m$, $R^n$, $R^{16a}$, $R^{16b}$, $R^{7a}$, $R^{7b}$, $R^{12a}$, $R^{12b}$, $R^{11a}$, $R^{11b}$, $R^{2a}$, $R^{2b}$, $R^{19}$, $R^{4a}$, and $R^{4b}$ and $R^{4b}$ are hydrogen, then $R^{3a}$ is $C_1$-$C_6$ alkyl substituted with 1 or more independent occurrences of deuterium or $X^2$—$OX^3$, wherein $X^2$ and $X^3$ must be substituted with at least one occurrence of deuterium.

In some embodiments, R3a is C1-C3 alkyl substituted with 0-7 independent occurrences of deuterium or X2a—OX3a, wherein X2a is C1-C3 alkylene substituted with 0-7 independent occurrences of deuterium and X3a is C1-C3 alkylene substituted with 0-7 independent occurrences of deuterium. In some embodiments, if R3a is CH3, then at least one of R5, R6a, R6b, R17, R21a, R21b, R‴, and R″ is deuterium, or if all of R5, R6a, R6b, R17, R21a, R21b, Rm, and Rn are hydrogen, then R3a is a methyl group substituted with 1-3 independent occurrences of deuterium. In some embodiments, R3a is selected from the group consisting of —CH3 and —CD3. In some embodiments, R3a is —CH3. In some embodiments, R3a is —CD3. In some embodiments, at least one of R5, R6a, R6b, R17, R21a, R21b, Rm, Rn, R16a, R16b, R7a, R7b, R12a, R12b, R11a, R11b, R2a, R2b, R19, R4a, and R4b is deuterium. In some embodiments, at least one of R5, R6a, R6b, R17, R21a, R21b, Rm, and Rn is deuterium. In some embodiments, R3a is —CH3 and at least one of R5, R6a, R6b, R17, R21a, R21b, Rm, Rn, R16a, R16b, R7a, R7b, R12a, R12b, R11a, R11b, R2a, R2b, R19, R4a, and R4b is deuterium. In some embodiments, R3a is —CH3 and at least one of R5, R6a, R6b, R17, R21a, R21b, Rm, and Rn is deuterium. In some embodiments, R5 and R6a are hydrogen. In some embodiments, R5 and R6a are deuterium. In some embodiments, R17 is hydrogen. In some embodiments, R17 is deuterium. In some embodiments, each of R21a and R21b is independently selected from the group consisting of hydrogen and deuterium. In some embodiments, R21a and R21b are hydrogen. In some embodiments, R21a and R21b are deuterium. In some embodiments, Rm and Rn are hydrogen. In some embodiments, Rm and Rn are deuterium. In some embodiments, R21a, R21b, Rm, and Rn are deuterium. In some embodiments, R17 and R16a are deuterium and R16b is hydrogen. In some embodiments, R19 is hydrogen.

In some embodiments, the compound of Formula (I) is the compound of Formula (I-A)

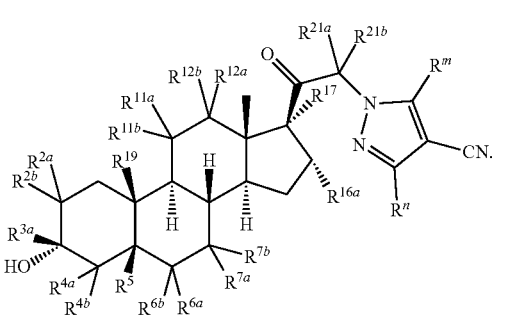

(I-A)

In some embodiments, the compound of Formula (I) is the compound of Formula (I-B)

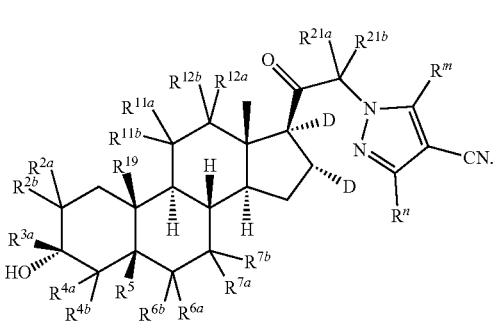

(I-B)

In some embodiments, the compound of Formula (I) is the compound of Formula (I-C)

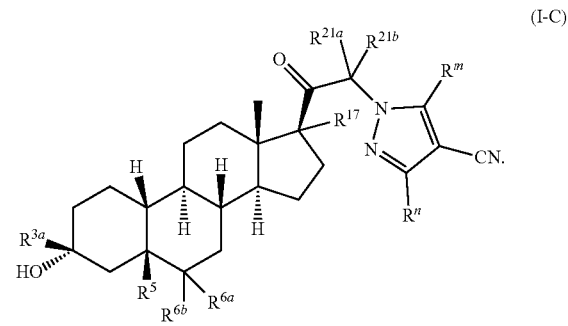

(I-C)

In some embodiments, the compound of Formula (I-C) is selected from the group consisting of the compounds identified in Table 1 below:

TABLE 1

| Compound Number | $R^{3a}$ | $R^5$ | $R^{6a}$ | $R^{6b}$ | $R^{17}$ | $R^{21a}$ | $R^{21b}$ | $R^m$ | $R^n$ |
|---|---|---|---|---|---|---|---|---|---|
| 1 | CD3 | H | H | H | H | H | H | H | H |
| 2 | CH3 | D | D | H | H | H | H | H | H |
| 3 | CH3 | H | H | H | D | H | H | H | H |
| 4 | CH3 | H | H | H | H | D | D | H | H |
| 5 | CH3 | H | H | H | H | H | H | D | D |
| 6 | CD3 | H | H | H | D | D | D | D | D |
| 7 | CH3 | H | H | H | D | D | D | D | D |
| 8 | CD3 | H | H | H | H | H | H | D | D | wherein any atom not labeled as deuterium is present at its natural isotopic abundance.

In one aspect, provided herein is a pharmaceutically acceptable salt of a compound described herein (e.g., a compound of Formula (I)).

In one aspect, provided herein is a pharmaceutical composition comprising a compound described herein (e.g., a compound of Formula (I)) or a pharmaceutically acceptable salt thereof, and a pharmaceutically acceptable excipient. In certain embodiments, the compound of the present invention is provided in an effective amount in the pharmaceutical composition. In certain embodiments, the compound of the present invention is provided in a therapeutically effective amount.

Compounds of the present invention as described herein, act, in certain embodiments, as GABA modulators, e.g., effecting the GABAA receptor in either a positive or negative manner. As modulators of the excitability of the central nervous system (CNS), as mediated by their ability to modulate GABAA receptor, such compounds are expected to have CNS-activity.

Thus, in another aspect, provided are methods of treating a CNS-related disorder in a subject in need thereof, comprising administering to the subject an effective amount of a compound of the present invention. In certain embodiments, CNS-related disorder is a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, tinnitus, or status epilepticus. In certain embodiments, the CNS-related disorder is depression. In certain embodiments, the CNS-related disorder is postpartum depression. In certain embodiments, the CNS-related disorder is major depressive disorder. In certain embodiments, the major depressive disorder is moderate major depressive disorder. In certain embodiments, the major depressive disorder is severe major depressive disorder. In certain embodiments, the compound is administered orally, subcutaneously, intravenously, or intramuscularly. In certain embodiments, the compound is administered orally. In certain embodiments, the compound is administered chronically. In certain embodiments, the compound is administered continuously, e.g., by continuous intravenous infusion.

DETAILED DESCRIPTION OF CERTAIN EMBODIMENTS OF THE INVENTION

As generally described herein, the present invention provides deuterium-enriched neuroactive steroids designed, for example, to act as GABA modulators. In certain embodiments, such compounds are envisioned to be useful as therapeutic agents for treating a CNS-related disorder (e.g., a disorder as described herein, for example depression, such as post-partum depression or major depressive disorder).

Definitions

Chemical Definitions

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, March's Advanced Organic Chemistry, 5th Edition, John Wiley & Sons, Inc., New York, 2001; Larock, Comprehensive Organic Transformations, VCH Publishers, Inc., New York, 1989; and Carruthers, Some Modern Methods of Organic Synthesis, 3rd Edition, Cambridge University Press, Cambridge, 1987.

Compounds described herein (e.g., a compound of Formula (I), e.g., a compound of Formula (I)) are deuterium-enriched.

Deuterium (D or 2H) is a stable, non-radioactive isotope of hydrogen and has an atomic weight of 2.0144. Hydrogen naturally occurs as a mixture of the isotopes 1H (hydrogen or protium), D (2H or deuterium), and T (3H or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015% should be considered unnatural and, as a result, novel over their non-enriched counterparts.

The effects of deuterium modification on a compound's metabolic properties are not predictable, even when deuterium atoms are incorporated at known sites of metabolism. Only by actually preparing and testing a deuterated compound can one determine if and how the rate of metabolism will differ from that of its non-deuterated counterpart. See, for example, Fukuto et al. (J. Med. Chem. 1991, 34, 2871-76). Many compounds have multiple sites where metabolism is possible. The site(s) where deuterium substitution is required and the extent of deuteration necessary to see an effect on metabolism, if any, will be different for each compound.

Unless otherwise stated, when a position is designated specifically as "H" or "hydrogen," the position is understood to have hydrogen (i.e., 1H) at its natural abundance isotopic composition. Also unless otherwise stated, when a position is designated specifically as "D" or "deuterium," the position is understood to have deuterium (i.e., 2H) at an abundance that is at least 3000 times greater than the natural abundance of deuterium, which is 0.015% (i.e., the term "D" or "deuterium" indicates at least 45% incorporation of deuterium).

The term "isotopic enrichment factor" as used herein means the ratio between the isotopic abundance of D at the specified position in a compound of this invention and the naturally occurring abundance of that isotope.

Increasing the amount of deuterium present in a compound (e.g., a compound of Formula (I)) is called "deuterium-enrichment," and such compounds are referred to as "deuterium-enriched" compounds. If not specifically noted, the percentage of enrichment refers to the percentage of deuterium present in the compound.

In other embodiments, a compound of this invention has an isotopic enrichment factor for each deuterium present at a site designated at a potential site of deuteration on the compound of at least 3500 (52.5.% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6466.7 (97% deuterium incorporation), at least 6633.3 (99.5% deuterium incorporation). It is understood that the isotopic enrichment factor of each deuterium present at a site designated as a site of deuteration is independent of other deuterated sites. For example, if there are two sites of deuteration on a compound one site could be deuterated at 52.5% while the other could be deuterated at 75%. The resulting compound would be considered to be a compound wherein the isotopic enrichment factor is at least 3500 (52.5%).

Because the natural abundance of deuterium is about 0.015%, approximately one in every 6,667 naturally occurring sites of hydrogen in a compound described herein, e.g., a compound of Formula (I), would be expected to have a deuterium present.

All percentages given for the amount of deuterium present are mole percentages.

It can be difficult in the laboratory to achieve 100% deuteration at any one site of a lab scale amount of compound (e.g., milligram or greater). When 100% deuteration is recited or a deuterium atom is specifically shown in a structure, it is assumed that a small percentage of hydrogen may still be present. Deuterium-enriched can be achieved by either exchanging protons with deuterium or by synthesizing the molecule with enriched starting materials.

Also described herein is the isolation or purification of deuterium-enriched compounds of Formula (I). The isolated or purified deuterium-enriched compounds of Formula (I).

Isomers, e.g., stereoisomers, can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, Stereochemistry of Carbon Compounds (McGraw-Hill, NY, 1962); and Wilen, Tables of Resolving Agents and Optical Resolutions p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The term "diastereomerically pure" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of a single diastereomer. Methods for determining diastereomeric and enantiomeric purity are well-known in the art. Diastereomeric purity can be determined by any analytical method capable of quantitatively distinguishing between a compound and its diastereomers, such as high performance liquid chromatography (HPLC).

The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example "C1-6 alkyl" is intended to encompass, C1, C2, C3, C4, C5, C6, C1-6, C1-5, C1-4, C1-3, C1-2, C2-6, C2-5, C2-4, C2-3, C3-6, C3-5, C3-4, C4-6, C4-5, and C5-6 alkyl. C2-5

The following terms are intended to have the meanings presented therewith below and are useful in understanding the description and intended scope of the present invention.

"Alkyl" refers to a radical of a straight-chain or branched saturated hydrocarbon group having 1 to 4 carbon atoms ("C1-4 alkyl"). In some embodiments, an alkyl group has 1 to 3 carbon atoms ("C1-3 alkyl"). In some embodiments, an alkyl group has 1 to 2 carbon atoms ("C1-2 alkyl"). In some embodiments, an alkyl group has 1 carbon atom ("C1 alkyl"). Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 3 substituents, or 1 substituent. In certain embodiments, the alkyl group is unsubstituted C1-4 alkyl (e.g., —CH3). In certain embodiments, the alkyl group is substituted C1-4 alkyl. Common alkyl abbreviations include Me (—CH3), Et (—CH2CH3), or iPr (—CH(CH3)2).

A "counterion" or "anionic counterion" is a negatively charged group associated with a cationic quaternary amino group in order to maintain electronic neutrality. Exemplary counterions include halide ions (e.g., F−, Cl−, Br−, I−), NO3−, ClO4−, OH—, H2PO4−, HSO4−, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

These and other exemplary substituents are described in more detail in the Detailed Description, and Claims. The invention is not intended to be limited in any manner by the above exemplary listing of substituents.

Other Definitions

As used herein, the term "modulation" refers to the inhibition or potentiation of GABA receptor function. A "modulator" (e.g., a modulator compound) may be, for example, an agonist, partial agonist, antagonist, or partial antagonist of the GABA receptor.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term "pharmaceutically acceptable cation" refers to an acceptable cationic counterion of an acidic functional group. Such cations are exemplified by sodium, potassium, calcium, magnesium, ammonium, tetraalkylammonium cations, and the like. See, e.g., Berge, et al., J. Pharm. Sci. (1977) 66(1): 1-79.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity of the subject.

In some embodiments, the compound of Formula (I) is a prodrug, wherein the prodrug includes a cleavable moiety on the C3 hydroxy as depicted in Formula (I). Exemplary hydroxyl containing prodrugs include, for example, esters.

"Solvate" refers to forms of the compound that are associated with a solvent or water (also referred to as "hydrate"), usually by a solvolysis reaction. This physical association includes hydrogen bonding. Conventional solvents include water, ethanol, acetic acid, and the like. The compounds of the invention may be prepared e.g. in crystalline form and may be solvated or hydrated. Suitable solvates include pharmaceutically acceptable solvates, such as hydrates, and further include both stoichiometric solvates and nonstoichiometric solvates. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

"Stereoisomers": It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition.

In general, the "effective amount" of a compound refers to an amount sufficient to elicit the desired biological response, e.g., to treat a CNS-related disorder, is sufficient to induce anesthesia or sedation. As will be appreciated by those of ordinary skill in this art, the effective amount of a compound of the invention may vary depending on such factors as the desired biological endpoint, the pharmacokinetics of the compound, the disease being treated, the mode of administration, and the age, weight, health, and condition of the subject.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

In an alternative embodiment, compounds of Formula (I) or a pharmaceutically acceptable salt or a pharmaceutically acceptable composition thereof, can also be administered in a "prophylactically effective amount". As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

Compounds

In one aspect, provided herein is a compound of Formula (I):

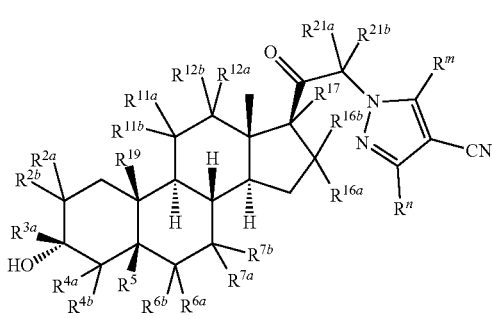

or a pharmaceutically acceptable salt thereof, wherein $R^{3a}$ is $C_1$-$C_6$ alkyl optionally substituted with 1 or more independent occurrences of deuterium or $X^2$—$OX^3$, wherein each of $X^2$ and $X^3$ is independently a $C_1$-$C_6$ alkylene optionally substituted with 1 more occurrences of deuterium; and each of $R^5$, $R^{6a}$, $R^{6b}$, $R^{17}$, $R^{21a}$, $R^{21b}$, $R^m$, $R^n$, $R^{16a}$, $R^{16b}$, $R^{7a}$, $R^{7b}$, $R^{12a}$, $R^{12b}$, $R^{11a}$, $R^{11b}$, $R^{2a}$, $R^{2b}$, $R^{19}$, $R^{4a}$, and $R^{4b}$ is independently selected from the group consisting of hydrogen and deuterium, provided that (a) if $R^{3a}$ is $C_1$-$C_6$ alkyl with no occurrences of deuterium or $X^2$—$OX^3$, wherein each of $X^2$ and $X^3$ is independently an $C_1$-$C_6$ alkylene with no occurrences of deuterium, then at least one of $R^5$, $R^{6a}$, $R^{6b}$, $R^{17}$, $R^{21a}$, $R^{21b}$, $R^m$, and $R^n$, $R^{16a}$, $R^{16b}$, $R^{7a}$, $R^{7b}$, $R^{12a}$, $R^{12b}$, $R^{11a}$, $R^{11b}$, $R^{2a}$, $R^{2b}$, $R^{19}$, $R^{4a}$, and $R^{4b}$ is deuterium, or (b) if all of $R^5$, $R^{6a}$, $R^{6b}$, $R^{17}$, $R^{21a}$, $R^{21b}$, $R^m$, $R^n$, $R^{16a}$, $R^{16b}$, $R^{7a}$, $R^{7b}$, $R^{12a}$, $R^{12b}$, $R^{11a}$, $R^{11b}$, $R^{2a}$, $R^{2b}$, $R^{19}$, $R^{4a}$, and $R^{4b}$ are hydrogen, then $R^{3a}$ is $C_1$-$C_6$ alkyl substituted with 1 or more independent occurrences of deuterium or $X^2$—$OX^3$, wherein $X^2$ and $X^3$ must be substituted with at least one occurrence of deuterium.

In some embodiments, R3a is C1-C3 alkyl substituted with 0-7 independent occurrences of deuterium or X2a—OX3a, wherein X2a is C1-C3 alkylene substituted with 0-7 independent occurrences of deuterium and X3a is C1-C3 alkylene substituted with 0-7 independent occurrences of deuterium. In some embodiments, if R3a is —CH3, then at least one of R5, R6a, R6b, R17, R21a, R21b, Rm, and Rn is deuterium, or if all of R5, R6a, R6b, R17, R21a, R21b, Rm, and Rn are hydrogen, then R3a is a methyl group substituted with 1-3 independent occurrences of deuterium. In some embodiments, R3a is selected from the group consisting of —CH3 and —CD3. In some embodiments, R3a is —CH3. In some embodiments, R3a is —CD3. In some embodiments, at least one of R5, R6a, R6b, R17, R21a, R21b, Rm, Rn, R16a, R16b, R7a, R7b, R12a, R12b, R11a, R11b, R2a, R2b, R19, R4a, and R4b is deuterium. In some embodiments, at least one of R5, R6a, R6b, R17, R21a, R21b, Rm, and Rn is deuterium. In some embodiments, R3a is —CH3 and at least one of R5, R6a, R6b, R17, R21a, R21b, Rm, Rn, R16a, R16b, R7a, R7b, R12a, R12b, R11a, R11b, R2a, R2b, R19, R4a, and R4b is deuterium. In some embodiments, R3a is —CH3 and at least one of R5, R6a, R6b, R17, R21a, R21b, Rm, and Rn is deuterium. In some embodiments, R5 and R6a are hydrogen. In some embodiments, R5 and R6a are deuterium. In some embodiments, R17 is hydrogen. In some embodiments, R17 is deuterium. In some embodiments, each of R21a and R21b is independently selected from the group consisting of hydrogen and deuterium. In some embodiments, R21a and R21b are hydrogen. In some embodiments, R21a and R21b are deuterium. In some embodiments, Rm and Rn are hydrogen. In some embodiments, Rm and Rn are deuterium. In some embodiments, R21a, R21b, Rm, and Rn are deuterium. In some embodiments, R17 and R16a are deuterium and R16b is hydrogen. In some embodiments, R19 is hydrogen.

In some embodiments, the compound of Formula (I) is the compound of Formula (I-A)

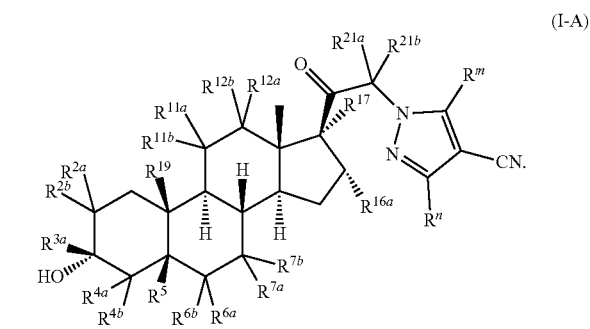

In some embodiments, the compound of Formula (I) is the compound of Formula (I-B)

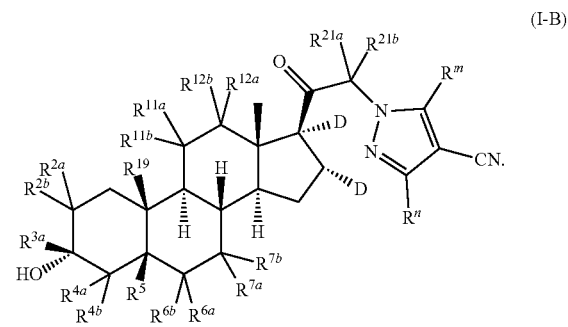

In some embodiments, the compound of Formula (I) is the compound of Formula (I-C)

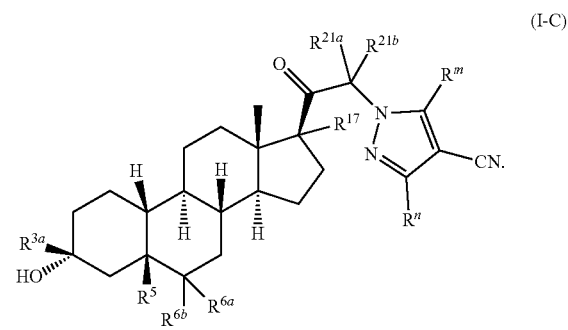

In some embodiments, the compound of Formula (I-C) is selected from the group consisting of the compounds identified in Table 1 below:

TABLE 1

| Compound Number | $R^{3a}$ | $R^5$ | $R^{6a}$ | $R^{6b}$ | $R^{17}$ | $R^{21a}$ | $R^{21b}$ | $R^m$ | $R^n$ |
|---|---|---|---|---|---|---|---|---|---|
| 1 | $CD_3$ | H | H | H | H | H | H | H | H |
| 2 | $CH_3$ | D | D | H | H | H | H | H | H |
| 3 | $CH_3$ | H | H | H | D | H | H | H | H |
| 4 | $CH_3$ | H | H | H | H | D | D | H | H |
| 5 | $CH_3$ | H | H | H | H | H | H | D | D |
| 6 | $CD_3$ | H | H | H | H | D | D | D | D |
| 7 | $CH_3$ | H | H | H | H | D | D | D | D |
| 8 | $CD_3$ | H | H | H | H | H | H | D | D | wherein any atom not labeled as deuterium is present at its natural isotopic abundance.

Exemplary compounds of the invention may be synthesized from the following known starting materials using methods known to one skilled in the art or certain references, e.g., U.S. Pat. No. 9,512,165, which is incorporated herein by reference:

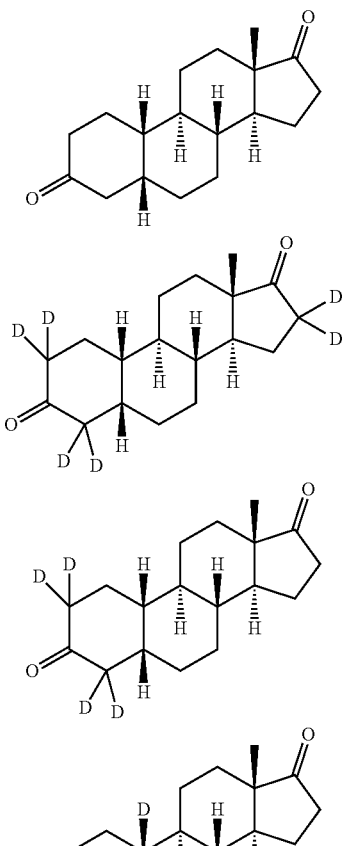

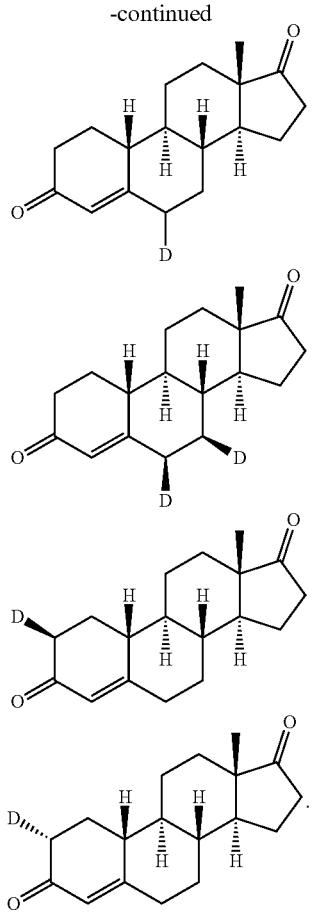

In some embodiments, the starting materials can be used to synthesize compounds of formula (I) wherein R3a is —CD3 and each of R21a, R21b, Rm, and Rn are independently hydrogen or deuterium. In some embodiments, the starting materials can be used to synthesize compounds of formula (I) wherein R3a is —CH3 and each of R21a, R21b, Rm, and Rn are independently hydrogen or deuterium. In some embodiments, the starting materials can be used to synthesize compounds of formula (I) wherein R3a is —CD3 and R21a, R21b are hydrogen and Rm and Rn are deuterium. In some embodiments, the starting materials can be used to synthesize compounds of formula (I) wherein R3a is CH3 and R21a, R21b are hydrogen and Rm and Rn are deuterium. In some embodiments, the starting materials can be used to synthesize compounds of formula (I) wherein R3a is —CD3 and R21a, R21b, Rm, and Rn are deuterium. In some embodiments, the starting materials can be used to synthesize compounds of formula (I) wherein R3a is —CH3 and R21a, R21b, Rm, and Rn are deuterium.

In one aspect, provided herein is a pharmaceutically acceptable salt of a compound described herein (e.g., a compound of Formula (I)).

Alternative Embodiments

In an alternative embodiment, compounds described herein may also comprise one or more isotopic substitutions of atoms other than hydrogen. For example, carbon may be, for example, 13C or 14C; oxygen may be, for example, 18O; nitrogen may be, for example, 15N, and the like. In other embodiments, a particular isotopte (e.g., 13C, 14C, 18O, or 15N) can represent at least 1%, at least 5%, at least 10%, at least 15%, at least 20%, at least 25%, at least 30%, at least 35%, at least 40%, at least 45%, at least 50%, at least at least 60%, at least 65%, at least 70%, at least 75%, at least 80%, at least 85%, at least 90%, at least 95%, at least 99%, or at least 99.9% of the total isotopic abundance of an element that occupies a specific site of the compound.

Pharmaceutical Compositions

In one aspect, provided herein is a pharmaceutical composition comprising a compound described herein (e.g., a compound of Formula (I)) or a pharmaceutically acceptable salt thereof, and a pharmaceutically acceptable excipient. In certain embodiments, the compound of the present invention is provided in an effective amount in the pharmaceutical composition. In certain embodiments, the compound of the present invention is provided in a therapeutically effective amount.

In certain embodiments, the pharmaceutical composition comprises an effective amount of the active ingredient. In certain embodiments, the pharmaceutical composition comprises a therapeutically effective amount of the active ingredient.

The pharmaceutical compositions provided herein can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compositions of the present invention may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, preferably from about 0.1 to about 20% by weight, preferably from about 0.1 to about 10% by weight, and more preferably from about 0.5 to about 15% by weight.

Injection dose levels range from about 0.1 mg/kg/hour to at least 20 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 5 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pennsylvania, which is incorporated herein by reference.

The compounds of the present invention can also be administered in sustained release forms or from sustained release drug delivery systems. A description of representative sustained release materials can be found in Remington's Pharmaceutical Sciences.

The present invention also relates to the pharmaceutically acceptable acid addition salt of a compound of the present invention. The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

In another aspect, the invention provides a pharmaceutical composition comprising a compound of the present invention and a pharmaceutically acceptable excipient, e.g., a composition suitable for injection, such as for intravenous (IV) administration.

Pharmaceutically acceptable excipients include any and all diluents or other liquid vehicles, dispersion or suspension aids, surface active agents, isotonic agents, preservatives, lubricants and the like, as suited to the particular dosage form desired, e.g., injection. General considerations in the formulation and/or manufacture of pharmaceutical compositions agents can be found, for example, in Remington's Pharmaceutical Sciences, Sixteenth Edition, E. W. Martin (Mack Publishing Co., Easton, Pa., 1980), and Remington: The Science and Practice of Pharmacy, 21st Edition (Lippincott Williams & Wilkins, 2005).

For example, injectable preparations, such as sterile injectable aqueous suspensions, can be formulated according to the known art using suitable dispersing or wetting agents and suspending agents. Exemplary excipients that can be employed include, but are not limited to, water, sterile saline or phosphate-buffered saline, or Ringer's solution.

In certain embodiments, the pharmaceutical composition further comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, substituted or unsubstituted methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as CAPTISOL®. See, e.g., U.S. Pat. No. 5,376,645. In certain embodiments, the composition comprises hexapropyl-β-cyclodextrin. In a more particular embodiment, the composition comprises hexapropyl-β-cyclodextrin (10-50% in water).

The injectable composition can be sterilized, for example, by filtration through a bacterial-retaining filter, or by incorporating sterilizing agents in the form of sterile solid compositions which can be dissolved or dispersed in sterile water or other sterile injectable medium prior to use.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, response of the individual patient, the severity of the patient's symptoms, and the like.

The compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include pre-filled, premeasured ampules or syringes of the liquid compositions. In such compositions, the compound is usually a minor component (from about 0.1% to about 50% by weight or preferably from about 1% to about 40% by weight) with the remainder being various vehicles or carriers and processing aids helpful for forming the desired dosing form.

The compounds provided herein can be administered as the sole active agent, or they can be administered in combination with other active agents. In one aspect, the present invention provides a combination of a compound of the present invention and another pharmacologically active agent. Administration in combination can proceed by any technique apparent to those of skill in the art including, for example, separate, sequential, concurrent, and alternating administration.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in Remington: The Science and Practice of Pharmacy 21st ed., Lippincott Williams & Wilkins, 2005.

In one aspect, provided is a kit comprising a composition (e.g., a solid composition) comprising a compound of Formula (I).

Methods of Use and Treatment

In an aspect, compounds described herein, e.g., compounds of Formula (I), are envisioned to be useful as therapeutic agents for treating a CNS-related disorder (e.g., sleep disorder, a mood disorder such as depression, a schizophrenia spectrum disorder, a convulsive disorder, epileptogenesis, a disorder of memory and/or cognition, a movement disorder, a personality disorder, autism spectrum disorder, pain, traumatic brain injury, a vascular disease, a substance abuse disorder and/or withdrawal syndrome, or tinnitus) in a subject in need (e.g., a subject with Rett syndrome, Fragile X syndrome, or Angelman syndrome). Exemplary CNS conditions related to GABA-modulation include, but are not limited to, sleep disorders [e.g., insomnia], mood disorders [e.g., depression, dysthymic disorder (e.g., mild depression), bipolar disorder (e.g., I and/or II), anxiety disorders (e.g., generalized anxiety disorder (GAD), social anxiety disorder), stress, post-traumatic stress disorder (PTSD), compulsive disorders (e.g., obsessive compulsive disorder (OCD))], schizophrenia spectrum disorders [e.g., schizophrenia, schizoaffective disorder], convulsive disorders [e.g., epilepsy (e.g., status epilepticus (SE)), seizures], disorders of memory and/or cognition [e.g., attention disorders (e.g., attention deficit hyperactivity disorder (ADHD)), dementia (e.g., Alzheimer's type dementia, Lewis body type dementia, vascular type dementia], movement disorders [e.g., Huntington's disease, Parkinson's disease], personality disorders [e.g., anti-social personality disorder, obsessive compulsive personality disorder], autism spectrum disorders (ASD) [e.g., autism, monogenetic causes of autism such as synaptophathy's, e.g., Rett syndrome, Fragile X syndrome, Angelman syndrome], pain [e.g., neuropathic pain, injury related pain syndromes, acute pain, chronic pain], traumatic brain injury (TBI), vascular diseases [e.g., stroke, ischemia, vascular malformations], substance abuse disorders and/or withdrawal syndromes [e.g., addition to opiates, cocaine, and/or alcohol], and tinnitus.

In certain embodiments, CNS-related disorder is a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, tinnitus, or status epilepticus. In certain embodiments, the CNS-related disorder is depression. In certain embodiments, the CNS-related disorder is postpartum depression. In certain embodiments, the CNS-related disorder is major depressive disorder. In certain embodiments, the major depressive disorder is moderate major depressive disorder. In certain embodiments, the major depressive disorder is severe major depressive disorder.

In an aspect, provided is a method of alleviating or preventing seizure activity in a subject, comprising administering to the subject in need of such treatment an effective amount of a compound of the present invention. In some embodiments, the method alleviates or prevents epileptogenesis.

In yet another aspect, provided is a combination of a compound of the present invention and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

In another aspect, provided is a method of treating or preventing brain excitability in a subject susceptible to or afflicted with a condition associated with brain excitability, comprising administering to the subject an effective amount of a compound of the present invention to the subject.

In yet another aspect, provided is a method of treating or preventing stress or anxiety in a subject, comprising administering to the subject in need of such treatment an effective amount of a compound of the present invention, or a composition thereof.

In yet another aspect, provided is a method of alleviating or preventing insomnia in a subject, comprising administering to the subject in need of such treatment an effective amount of a compound of the present invention, or a composition thereof.

In yet another aspect, provided is a method of inducing sleep and maintaining substantially the level of REM sleep that is found in normal sleep, wherein substantial rebound insomnia is not induced, comprising administering an effective amount of a compound of the present invention.

In yet another aspect, provided is a method of alleviating or preventing PMS or PND in a subject, comprising administering to the subject in need of such treatment an effective amount of a compound of the present invention.

In yet another aspect, provided is a method of treating or preventing mood disorders in a subject, comprising administering to the subject in need of such treatment an effective amount of a compound of the present invention. In certain embodiments the mood disorder is depression.

In yet another aspect, provided is a method of cognition enhancement or treating memory disorder by administering to the subject a therapeutically effective amount of a compound of the present invention. In certain embodiments, the disorder is Alzheimer's disease. In certain embodiments, the disorder is Rett syndrome.

In yet another aspect, provided is a method of treating attention disorders by administering to the subject a therapeutically effective amount of a compound of the present invention. In certain embodiments, the attention disorder is ADHD.

In certain embodiments, the compound is administered to the subject chronically. In certain embodiments, the compound is administered to the subject orally, subcutaneously, intramuscularly, or intravenously.

Neuroendocrine Disorders and Dysfunction

Provided herein are methods that can be used for treating neuroendocrine disorders and dysfunction. As used herein, "neuroendocrine disorder" or "neuroendocrine dysfunction" refers to a variety of conditions caused by imbalances in the body's hormone production directly related to the brain. Neuroendocrine disorders involve interactions between the nervous system and the endocrine system. Because the hypothalamus and the pituitary gland are two areas of the brain that regulate the production of hormones, damage to the hypothalamus or pituitary gland, e.g., by traumatic brain injury, may impact the production of hormones and other neuroendocrine functions of the brain. In some embodiments, the neuroendocrine disorder or dysfunction is associated with a women's health disorder or condition (e.g., a women's health disorder or condition described herein). In some embodiments, the neuroendocrine disorder or dysfunction is associated with a women's health disorder or condition is polycystic ovary syndrome.

Symptoms of neuroendocrine disorder include, but are not limited to, behavioral, emotional, and sleep-related symptoms, symptoms related to reproductive function, and somatic symptoms; including but not limited to fatigue, poor memory, anxiety, depression, weight gain or loss, emotional lability, lack of concentration, attention difficulties, loss of lipido, infertility, amenorrhea, loss of muscle mass, increased belly body fat, low blood pressure, reduced heart rate, hair loss, anemia, constipation, cold intolerance, and dry skin.

Neurodegenerative Diseases and Disorders

The methods described herein can be used for treating neurodegenerative diseases and disorders. The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; ataxia and convulsion (including for the treatment and prevention and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g., spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, Parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cycloclonus), tremor (such as rest tremor, postural tremor, and intention tremor) and dystonia (including axial dystonia, dystonic writer's cramp, hemiplegic dystonia, paroxysmal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; tubular sclerosis, and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest. Methods of treating or preventing a neurodegenerative disease also include treating or preventing loss of neuronal function characteristic of neurodegenerative disorder.

Mood Disorders

Also provided herein are methods for treating a mood disorder, for example clinical depression, postnatal depression or postpartum depression, perinatal depression, atypical depression, melancholic depression, psychotic major depression, catatonic depression, seasonal affective disorder, dysthymia, double depression, depressive personality disorder, recurrent brief depression, minor depressive disorder, bipolar disorder or manic depressive disorder, depression caused by chronic medical conditions, treatment-resistant depression, refractory depression, suicidality, suicidal ideation, or suicidal behavior. In some embodiments, the method described herein provides therapeutic effect to a subject suffering from depression (e.g., moderate or severe depression). In some embodiments, the mood disorder is associated with a disease or disorder described herein (e.g., neuroendocrine diseases and disorders, neurodegenerative diseases and disorders (e.g., epilepsy), movement disorders, tremor (e.g., Parkinson's Disease), women's health disorders or conditions).

Clinical depression is also known as major depression, major depressive disorder (MDD), severe depression, unipolar depression, unipolar disorder, and recurrent depression, and refers to a mental disorder characterized by pervasive and persistent low mood that is accompanied by low self-esteem and loss of interest or pleasure in normally enjoyable activities. Some people with clinical depression have trouble sleeping, lose weight, and generally feel agitated and irritable. Clinical depression affects how an individual feels, thinks, and behaves and may lead to a variety of emotional and physical problems. Individuals with clinical depression may have trouble doing day-to-day activities and make an individual feel as if life is not worth living.

Peripartum depression refers to depression in pregnancy. Symptoms include irritability, crying, feeling restless, trouble sleeping, extreme exhaustion (emotional and/or physical), changes in appetite, difficulty focusing, increased anxiety and/or worry, disconnected feeling from baby and/or fetus, and losing interest in formerly pleasurable activities.

Postnatal depression (PND) is also referred to as postpartum depression (PPD), and refers to a type of clinical depression that affects women after childbirth. Symptoms can include sadness, fatigue, changes in sleeping and eating habits, reduced sexual desire, crying episodes, anxiety, and irritability. In some embodiments, the PND is a treatment-resistant depression (e.g., a treatment-resistant depression as described herein). In some embodiments, the PND is refractory depression (e.g., a refractory depression as described herein).

In some embodiments, a subject having PND also experienced depression, or a symptom of depression during pregnancy. This depression is referred to herein as) perinatal depression. In an embodiment, a subject experiencing perinatal depression is at increased risk of experiencing PND.

Atypical depression (AD) is characterized by mood reactivity (e.g., paradoxical anhedonia) and positivity, significant weight gain or increased appetite. Patients suffering from AD also may have excessive sleep or somnolence (hypersomnia), a sensation of limb heaviness, and significant social impairment as a consequence of hypersensitivity to perceived interpersonal rejection.

Melancholic depression is characterized by loss of pleasure (anhedonia) in most or all activities, failures to react to pleasurable stimuli, depressed mood more pronounced than that of grief or loss, excessive weight loss, or excessive guilt.

Psychotic major depression (PMD) or psychotic depression refers to a major depressive episode, in particular of melancholic nature, where the individual experiences psychotic symptoms such as delusions and hallucinations.

Catatonic depression refers to major depression involving disturbances of motor behavior and other symptoms. An individual may become mute and stuporose, and either is immobile or exhibits purposeless or bizarre movements.

Seasonal affective disorder (SAD) refers to a type of seasonal depression wherein an individual has seasonal patterns of depressive episodes coming on in the fall or winter.

Dysthymia refers to a condition related to unipolar depression, where the same physical and cognitive problems are evident. They are not as severe and tend to last longer (e.g., at least 2 years).

Double depression refers to fairly depressed mood (dysthymia) that lasts for at least 2 years and is punctuated by periods of major depression.

Depressive Personality Disorder (DPD) refers to a personality disorder with depressive features.

Recurrent Brief Depression (RBD) refers to a condition in which individuals have depressive episodes about once per month, each episode lasting 2 weeks or less and typically less than 2-3 days.

Minor depressive disorder or minor depression refers to a depression in which at least 2 symptoms are present for 2 weeks.

Bipolar disorder or manic depressive disorder causes extreme mood swings that include emotional highs (mania or hypomania) and lows (depression). During periods of mania the individual may feel or act abnormally happy, energetic, or irritable. They often make poorly thought out decisions with little regard to the consequences. The need for sleep is usually reduced. During periods of depression there may be crying, poor eye contact with others, and a negative outlook on life. The risk of suicide among those with the disorder is high at greater than 6% over 20 years, while self harm occurs in 30-40%. Other mental health issues such as anxiety disorder and substance use disorder are commonly associated with bipolar disorder.

Depression caused by chronic medical conditions refers to depression caused by chronic medical conditions such as cancer or chronic pain, chemotherapy, chronic stress.

Treatment-resistant depression refers to a condition where the individuals have been treated for depression, but the symptoms do not improve. For example, antidepressants or physchological counseling (psychotherapy) do not ease depression symptoms for individuals with treatment-resistant depression. In some cases, individuals with treatment-resistant depression improve symptoms, but come back. Refractory depression occurs in patients suffering from depression who are resistant to standard pharmacological treatments, including tricyclic antidepressants, MAOIs, SSRIs, and double and triple uptake inhibitors and/or anxiolytic drugs, as well as non-pharmacological treatments (e.g., psychotherapy, electroconvulsive therapy, vagus nerve stimulation and/or transcranial magnetic stimulation).

Post-surgical depression refers to feelings of depression that follow a surgical procedure (e.g., as a result of having to confront one's mortality). For example, individuals may feel sadness or empty mood persistently, a loss of pleasure or interest in hobbies and activities normally enjoyed, or a persistent feeling of worthlessness or hopelessness.

Mood disorder associated with conditions or disorders of women's health refers to mood disorders (e.g., depression) associated with (e.g., resulting from) a condition or disorder of women's health (e.g., as described herein).

Suicidality, suicidal ideation, suicidal behavior refers to the tendency of an individual to commit suicide. Suicidal ideation concerns thoughts about or an unusual preoccupation with suicide. The range of suicidal ideation varies greatly, from e.g., fleeting thoughts to extensive thoughts, detailed planning, role playing, incomplete attempts. Symptoms include talking about suicide, getting the means to commit suicide, withdrawing from social contact, being preoccupied with death, feeling trapped or hopeless about a situation, increasing use of alcohol or drugs, doing risky or self-destructive things, saying goodbye to people as if they won't be seen again.

Symptoms of depression include persistent anxious or sad feelings, feelings of helplessness, hopelessness, pessimism, worthlessness, low energy, restlessness, difficulty sleeping, sleeplessness, irritability, fatigue, motor challenges, loss of interest in pleasurable activities or hobbies, loss of concentration, loss of energy, poor self-esteem, absence of positive thoughts or plans, excessive sleeping, overeating, appetite loss, insomnia, self-harm, thoughts of suicide, and suicide attempts. The presence, severity, frequency, and duration of symptoms may vary on a case to case basis. Symptoms of depression, and relief of the same, may be ascertained by a physician or psychologist (e.g., by a mental state examination).

In some embodiments, the method comprises monitoring a subject with a known depression scale, e.g., the Hamilton Depression (HAM-D) scale, the Clinical Global Impression-Improvement Scale (CGI), and the Montgomery-Asberg Depression Rating Scale (MADRS). In some embodiments, a therapeutic effect can be determined by reduction in Hamilton Depression (HAM-D) total score exhibited by the subject. Reduction in the HAM-D total score can happen within 4, 3, 2, or 1 days; or 96, 84, 72, 60, 48, 24, 20, 16, 12, 10, 8 hours or less. The therapeutic effect can be assessed across a specified treatment period. For example, the therapeutic effect can be determined by a decrease from baseline in HAM-D total score after administering a compound described herein, e.g., a compound of Formula (I) (e.g., 12, 24, or 48 hours after administration; or 24, 48, 72, or 96 hours or more; or 1 day, 2 days, 14 days, 21 days, or 28 days; or 1 week, 2 weeks, 3 weeks, or 4 weeks; or 1 month, 2 months, 6 months, or 10 months; or 1 year, 2 years, or for life).

In some embodiments, the subject has a mild depressive disorder, e.g., mild major depressive disorder. In some embodiments, the subject has a moderate depressive disorder, e.g., moderate major depressive disorder. In some embodiments, the subject has a severe depressive disorder, e.g., severe major depressive disorder. In some embodiments, the subject has a very severe depressive disorder, e.g., very severe major depressive disorder. In some embodiments, the baseline HAM-D total score of the subject (i.e., prior to treatment with a compound described herein, e.g., a compound of Formula (I)) is at least 24. In some embodiments, the baseline HAM-D total score of the subject is at least 18. In some embodiments, the baseline HAM-D total score of the subject is between and including 14 and 18. In some embodiments, the baseline HAM-D total score of the subject is between and including 19 and 22. In some embodiments, the HAM-D total score of the subject before treatment with a compound described herein, e.g., a compound of Formula (I), is greater than or equal to 23. In some embodiments, the baseline score is at least 10, 15, or 20. In some embodiments, the HAM-D total score of the subject after treatment with a compound described herein, e.g., a compound of Formula (I), is about 0 to 10 (e.g., less than 10; 0 to 10, 0 to 6, 0 to 4, 0 to 3, 0 to 2, or 1.8). In some embodiments, the HAM-D total score after treatment with a compound described herein, e.g., a compound of Formula (I), is less than 10, 7, 5, or 3. In some embodiments, the decrease in HAM-D total score is from a baseline score of about 20 to 30 (e.g., 22 to 28, 23 to 27, 24 to 27, 25 to 27, 26 to 27) to a HAM-D total score at about 0 to 10 (e.g., less than 10; 0 to 10, 0 to 6, 0 to 4, 0 to 3, 0 to 2, or 1.8) after treatment with a compound described herein, e.g., a compound of Formula (I). In some embodiments, the decrease in the baseline HAM-D total score to HAM-D total score after treatment with a compound described herein, e.g., a compound of Formula (I), is at least 1, 2, 3, 4, 5, 7, 10, 25, 40, 50, or 100 fold). In some embodiments, the percentage decrease in the baseline HAM-D total score to HAM-D total score after treatment with a compound described herein, e.g., a compound of Formula (I), is at least 50% (e.g., 60%, 70%, 80%, or 90%). In some embodiments, the therapeutic effect is measured as a decrease in the HAM-D total score after treatment with a compound described herein, e.g., a compound of Formula (I), relative to the baseline HAM-D total score (e.g., 12, 24, 48 hours after administration; or 24, 48, 72, 96 hours or more; or 1 day, 2 days, 14 days, or more) is at least 10, 15, or 20 points.

In some embodiments, the method of treating a depressive disorder, e.g., major depressive disorder provides a therapeutic effect (e.g., as measured by reduction in Hamilton Depression Score (HAM-D)) within 14, 10, 4, 3, 2, or 1 days, or 24, 20, 16, 12, 10, or 8 hours or less. In some embodiments, the method of treating the depressive disorder, e.g., major depressive disorder, provides a therapeutic effect (e.g., as determined by a statistically significant reduction in HAM-D total score) within the first or second day of the treatment with a compound described herein, e.g., a compound of Formula (I). In some embodiments, the method of treating the depressive disorder, e.g., major depressive disorder, provides a therapeutic effect (e.g., as determined by a statistically significant reduction in HAM-D total score) within less than or equal to 14 days since the beginning of the treatment with a compound described herein, e.g., a compound of Formula (I). In some embodiments, the method of treating the depressive disorder, e.g., major depressive disorder, provides a therapeutic effect (e.g., as determined by a statistically significant reduction in HAM-D total score) within less than or equal to 21 days since the beginning of the treatment with a compound described herein, e.g., a compound of Formula (I). In some embodiments, the method of treating the depressive disorder, e.g., major depressive disorder, provides a therapeutic effect (e.g., as determined by a statistically significant reduction in HAM-D total score) within less than or equal to 28 days since the beginning of the treatment with a compound described herein, e.g., a compound of Formula (I). In some embodiments, the therapeutic effect is a decrease from baseline in HAM-D total score after treatment with a compound described herein, e.g., a compound of Formula (I) (e.g., treatment with a compound described herein, e.g., a compound of Formula (I), once a day for 14 days). In some embodiments, the HAM-D total score of the subject before treatment with a compound described herein, e.g., a compound of Formula (I), is at least 24. In some embodiments, the HAM-D total score of the subject before treatment with a compound described herein, e.g., a compound of Formula (I), is at least 18. In some embodiments, the HAM-D total score of the subject before treatment with a compound described herein, e.g., a compound of Formula (I), is between and including 14 and 18. In some embodiments, the decrease in HAM-D total score after treating the subject with a compound described herein, e.g., a compound of Formula (I), relative to the baseline HAM-D total score is at least 10. In some embodiments, the decrease in HAM-D total score after treating the subject with a compound described herein, e.g., a compound of Formula (I), relative to the baseline HAM-D total score is at least 15 (e.g., at least 17). In some embodiments, the HAM-D total score associated with treating the subject with a compound described herein, e.g., a compound of Formula (I), is no more than a number ranging from 6 to 8. In some embodiments, the HAM-D total score associated with treating the subject with a compound described herein, e.g., a compound of Formula (I), is no more than 7.

In some embodiments, the method provides therapeutic effect (e.g., as measured by reduction in Clinical Global Impression-Improvement Scale (CGI)) within 14, 10, 4, 3, 2, or 1 days, or 24, 20, 16, 12, 10, or 8 hours or less. In some embodiments, the CNS-disorder is a depressive disorder, e.g., major depressive disorder. In some embodiments, the method of treating the depressive disorder, e.g., major depressive disorder provides a therapeutic effect within the second day of the treatment period. In some embodiments, the therapeutic effect is a decrease from baseline in CGI score at the end of a treatment period (e.g., 14 days after administration).

In some embodiments, the method provides therapeutic effect (e.g., as measured by reduction in Montgomery-Asberg Depression Rating Scale (MADRS)) within 14, 10, 4, 3, 2, or 1 days, or 24, 20, 16, 12, 10, or 8 hours or less. In some embodiments, the CNS-disorder is a depressive disorder, e.g., major depressive disorder. In some embodiments, the method of treating the depressive disorder, e.g., major depressive disorder provides a therapeutic effect within the second day of the treatment period. In some embodiments, the therapeutic effect is a decrease from baseline in MADRS score at the end of a treatment period (e.g., 14 days after administration).

A therapeutic effect for major depressive disorder can be determined by a reduction in Montgomery-Asberg Depression Rating Scale (MADRS) score exhibited by the subject. For example, the MADRS score can be reduced within 4, 3, 2, or 1 days; or 96, 84, 72, 60, 48, 24, 20, 16, 12, 10, 8 hours or less. The Montgomery-Asberg Depression Rating Scale (MADRS) is a ten-item diagnostic questionnaire (regarding apparent sadness, reported sadness, inner tension, reduced sleep, reduced appetite, concentration difficulties, lassitude, inability to feel, pessimistic thoughts, and suicidal thoughts) which psychiatrists use to measure the severity of depressive episodes in patients with mood disorders.

In some embodiments, the method provides therapeutic effect (e.g., as measured by reduction in Edinburgh Postnatal Depression Scale (EPDS)) within 4, 3, 2, 1 days; 24, 20, 16, 12, 10, 8 hours or less. In some embodiments, the therapeutic effect is a improvement measured by the EPDS.

In some embodiments, the method provides therapeutic effect (e.g., as measured by reduction in Generalized Anxiety Disorder 7-Item Scale (GAD-7)) within 4, 3, 2, 1 days; 24, 20, 16, 12, 10, 8 hours or less.

Anxiety Disorders

Provided herein are methods for treating anxiety disorders (e.g., generalized anxiety disorder, panic disorder, obsessive compulsive disorder, phobia, post-traumatic stress disorder). Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

Women's Health Disorders

Provided herein are methods for treating conditions or disorders related to women's health. Conditions or disorders related to women's health include, but are not limited to, gynecological health and disorders (e.g., premenstrual syndrome (PMS), premenstrual dysphoric disorder (PMDD)), pregnancy issues (e.g., miscarriage, abortion), infertility and related disorders (e.g., polycystic ovary syndrome (PCOS)), other disorders and conditions, and issues related to women's overall health and wellness (e.g., menopause).

Gynecological health and disorders affecting women include menstruation and menstrual irregularities; urinary tract health, including urinary incontinence and pelvic floor disorders; and such disorders as bacterial vaginosis, vaginitis, uterine fibroids, and vulvodynia.

Premenstrual syndrome (PMS) refers to physical and emotional symptoms that occur in the one to two weeks before a women's period. Symptoms vary but can include bleeding, mood swings, tender breasts, food cravings, fatigue, irritability, acne, and depression.

Premenstrual dysphoric disorder (PMDD) is a severe form of PMS. The symptoms of PMDD are similar to PMS but more severe and may interfere with work, social activity, and relationships. PMDD symptoms include mood swings, depressed mood or feelings of hopelessness, marked anger, increased interpersonal conflicts, tension and anxiety, irritability, decreased interest in usual activities, difficulty concentrating, fatigue, change in appetite, feeling out of control or overwhelmed, sleep problems, physical problems (e.g., bloating, breast tenderness, swelling, headaches, joint or muscle pain).

Pregnancy issues include preconception care and prenatal care, pregnancy loss (miscarriage and stillbirth), preterm labor and premature birth, sudden infant death syndrome (SIDS), breastfeeding, and birth defects.

Miscarriage refers to a pregnancy that ends on its own, within the first 20 weeks of gestation.

Abortion refers to the deliberate termination of a pregnancy, which can be performed during the first 28 weeks of pregnancy.

Infertility and related disorders include uterine fibroids, polycystic ovary syndrome, endometriosis, and primary ovarian insufficiency.

Polycystic ovary syndrome (PCOS) refers to an endocrine system disorder among women of reproductive age. PCOS is a set of symptoms resulting from an elevated male hormone in women. Most women with PCOS grow many small cysts on their ovaries. Symptoms of PCOS include irregular or no menstrual periods, heavy periods, excess body and facial hair, acne, pelvic pain, difficulty getting pregnant, and patches of thick, darker, velvety skin. PCOS may be associated with conditions including type 2 diabetes, obesity, obstructive sleep apnea, heart disease, mood disorders, and endometrial cancer.

Other disorders and conditions that affect only women include Turner syndrome, Rett syndrome, and ovarian and cervical cancers.

Issues related to women's overall health and wellness include violence against women, women with disabilities and their unique challenges, osteoporosis and bone health, and menopause.

Menopause refers to the 12 months after a woman's last menstrual period and marks the end of menstrual cycles. Menopause typically occurs in a woman's 40s or 50s. Physical symptoms such as hot flashes and emotional symptoms of menopause may disrupt sleep, lower energy, or trigger anxiety or feelings of sadness or loss. Menopause includes natural menopause and surgical menopause, which is a type of induced menopause due to an event such as surgery (e.g., hysterectomy, oophorectomy; cancer). It is induced when the ovaries are gravely damaged by, e.g., radiation, chemotherapy, or other medications.

Epilepsy

The compound of Formula (I), or pharmaceutically acceptable salt, or a pharmaceutically acceptable composition thereof, can be used in a method described herein, for example in the treatment of a disorder described herein such as epilepsy, status epilepticus, or seizure.

Epilepsy is a brain disorder characterized by repeated seizures over time. Types of epilepsy can include, but are not limited to generalized epilepsy, e.g., childhood absence epilepsy, juvenile nyoclonic epilepsy, epilepsy with grand-mal seizures on awakening, West syndrome, Lennox-Gastaut syndrome, partial epilepsy, e.g., temporal lobe epilepsy, frontal lobe epilepsy, benign focal epilepsy of childhood.

Epileptogenesis

The compounds and methods described herein can be used to treat or prevent epileptogenesis. Epileptogenesis is a gradual process by which a normal brain develops epilepsy (a chronic condition in which seizures occur). Epileptogenesis results from neuronal damage precipitated by the initial insult (e.g., status epilepticus).

Status Epilepticus (SE)

Status epilepticus (SE) can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

Seizure

A seizure is the physical findings or changes in behavior that occur after an episode of abnormal electrical activity in the brain. The term "seizure" is often used interchangeably with "convulsion." Convulsions are when a person's body shakes rapidly and uncontrollably. During convulsions, the person's muscles contract and relax repeatedly.

Based on the type of behavior and brain activity, seizures are divided into two broad categories: generalized and partial (also called local or focal). Classifying the type of seizure helps doctors diagnose whether or not a patient has epilepsy.

Generalized seizures are produced by electrical impulses from throughout the entire brain, whereas partial seizures are produced (at least initially) by electrical impulses in a relatively small part of the brain. The part of the brain generating the seizures is sometimes called the focus.

There are six types of generalized seizures. The most common and dramatic, and therefore the most well known, is the generalized convulsion, also called the grand-mal seizure. In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand-mal seizures, injuries and accidents may occur, such as tongue biting and urinary incontinence.

Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of "losing time."

Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time.

Tonic seizures are characterized by stiffening of the muscles.

Atonic seizures consist of a sudden and general loss of muscle tone, particularly in the arms and legs, which often results in a fall.

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; atypical absence seizures; absence seizures; atonic seizures; benign Rolandic seizures; febrile seizures; emotional seizures; focal seizures; gelastic seizures; generalized onset seizures; infantile spasms; Jacksonian seizures; massive bilateral myoclonus seizures; multifocal seizures; neonatal onset seizures; nocturnal seizures; occipital lobe seizures; post traumatic seizures; subtle seizures; Sylvan seizures; visual reflex seizures; or withdrawal seizures. In some embodiments, the seizure is a generalized seizure associated with Dravet Syndrome, Lennox-Gastaut Syndrome, Tuberous Sclerosis Complex, Rett Syndrome or PCDH19 Female Pediatric Epilepsy.

The compound of Formula (I) or pharmaceutically acceptable salt, or a pharmaceutically acceptable composition thereof, can also be administered as a prophylactic to a subject having a CNS disorder e.g., a traumatic brain injury, status epilepticus, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges; prior to the onset of a seizure.

Movement Disorders

Also described herein are methods for treating a movement disorder. As used herein, "movement disorders" refers to a variety of diseases and disorders that are associated with hyperkinetic movement disorders and related abnormalities in muscle control. Exemplary movement disorders include, but are not limited to, Parkinson's disease and parkinsonism (defined particularly by bradykinesia), dystonia, chorea and Huntington's disease, ataxia, tremor (e.g., essential tremor), myoclonus and startle, tics and Tourette syndrome, Restless legs syndrome, stiff person syndrome, and gait disorders.

Tremor

The methods described herein can be used to treat tremor, for example the compound of Formula (I) can be used to treat cerebellar tremor or intention tremor, dystonic tremor, essential tremor, orthostatic tremor, parkinsonian tremor, physiological tremor, psychogenic tremor, or rubral tremor. Tremor includes hereditary, degenerative, and idiopathic disorders such as Wilson's disease, Parkinson's disease, and essential tremor, respectively; metabolic diseases (e.g., thyroid-parathyroid-, liver disease and hypoglycemia); peripheral neuropathies (associated with Charcot-Marie-Tooth, Roussy-Levy, diabetes mellitus, complex regional pain syndrome); toxins (nicotine, mercury, lead, CO, Manganese, arsenic, toluene); drug-induced (narcoleptics, tricyclics, lithium, cocaine, alcohol, adrenaline, bronchodilators, theophylline, caffeine, steroids, valproate, amiodarone, thyroid hormones, vincristine); and psychogenic disorders. Clinical tremor can be classified into physiologic tremor, enhanced physiologic tremor, essential tremor syndromes (including classical essential tremor, primary orthostatic tremor, and task- and position-specific tremor), dystonic tremor, parkinsonian tremor, cerebellar tremor, Holmes' tremor (i.e., rubral tremor), palatal tremor, neuropathic tremor, toxic or drug-induced tremor, and psychogenic tremor.

Tremor is an involuntary, at times rhythmic, muscle contraction and relaxation that can involve oscillations or twitching of one or more body parts (e.g., hands, arms, eyes, face, head, vocal folds, trunk, legs).

Cerebellar tremor or intention tremor is a slow, broad tremor of the extremities that occurs after a purposeful movement. Cerebellar tremor is caused by lesions in or damage to the cerebellum resulting from, e.g., tumor, stroke, disease (e.g., multiple sclerosis, an inherited degenerative disorder).

Dystonic tremor occurs in individuals affected by dystonia, a movement disorder in which sustained involuntary muscle contractions cause twisting and repetitive motions and/or painful and abnormal postures or positions. Dystonic tremor may affect any muscle in the body. Dystonic tremors occurs irregularly and often can be relieved by complete rest.

Essential tremor or benign essential tremor is the most common type of tremor. Essential tremor may be mild and nonprogressive in some, and may be slowly progressive, starting on one side of the body but affect both sides within 3 years. The hands are most often affected, but the head, voice, tongue, legs, and trunk may also be involved. Tremor frequency may decrease as the person ages, but severity may increase. Heightened emotion, stress, fever, physical exhaustion, or low blood sugar may trigger tremors and/or increase their severity. Symptoms generally evolve over time and can be both visible and persistent following onset.

Orthostatic tremor is characterized by fast (e.g., greater than 12 Hz) rhythmic muscle contractions that occurs in the legs and trunk immediately after standing. Cramps are felt in the thighs and legs and the patient may shake uncontrollably when asked to stand in one spot. Orthostatic tremor may occurs in patients with essential tremor.

Parkinsonian tremor is caused by damage to structures within the brain that control movement. Parkinsonian tremor is often a precursor to Parkinson's disease and is typically seen as a "pill-rolling" action of the hands that may also affect the chin, lips, legs, and trunk. Onset of parkinsonian tremor typically begins after age 60. Movement starts in one limb or on one side of the body and can progress to include the other side.

Physiological tremor can occur in normal individuals and have no clinical significance. It can be seen in all voluntary muscle groups. Physiological tremor can be caused by certain drugs, alcohol withdrawal, or medical conditions including an overactive thyroid and hypoglycemia. The tremor classically has a frequency of about 10 Hz.

Psychogenic tremor or hysterical tremor can occur at rest or during postural or kinetic movement. Patient with psychogenic tremor may have a conversion disorder or another psychiatric disease.

Rubral tremor is characterized by coarse slow tremor which can be present at rest, at posture, and with intention. The tremor is associated with conditions that affect the red nucleus in the midbrain, classical unusual strokes.

Parkinson's Disease affects nerve cells in the brain that produce dopamine. Symptoms include muscle rigidity, tremors, and changes in speech and gait. Parkinsonism is characterized by tremor, bradykinesia, rigidity, and postural instability. Parkinsonism shares symptoms found in Parkinson's Disease, but is a symptom complex rather than a progressive neurodegenerative disease.

Dystonia is a movement disorder characterized by sustained or intermittent muscle contractions causing abnormal, often repetitive movements or postures. Dystonic movements can be patterned, twisting, and may be tremulous. Dystonia is often initiated or worsened by voluntary action and associated with overflow muscle activation.

Chorea is a neurological disorder characterized by jerky involuntary movements typically affecting the shoulders, hips, and face. Huntington's Disease is an inherited disease that causes nerve cells in the brain to waste away. Symptoms include uncontrolled movements, clumsiness, and balance problems. Huntington's disease can hinder walk, talk, and swallowing.

Ataxia refers to the loss of full control of bodily movements, and may affect the fingers, hands, arms, legs, body, speech, and eye movements.

Myoclonus and Startle is a response to a sudden and unexpected stimulus, which can be acoustic, tactile, visual, or vestibular.

Tics are an involuntary movement usually onset suddenly, brief, repetitive, but non-rhythmical, typically imitating normal behavior and often occurring out of a background of normal activity. Tics can be classified as motor or vocal, motor tics associated with movements while vocal tics associated with sound. Tics can be characterized as simple or complex. For example simple motor tics involve only a few muscles restricted to a specific body part. Tourette Syndrome is an inherited neuropsychiatric disorder with onset in childhood, characterized by multiple motor tics and at least one vocal tic.

Restless Legs Syndrome is a neurologic sensorimotor disorder characterized by an overwhelming urge to move the legs when at rest.

Stiff Person Syndrome is a progressive movement disorder characterized by involuntary painful spasms and rigidity of muscles, usually involving the lower back and legs. Stiff-legged gait with exaggerated lumbar hyperlordosis typically results. Characteristic abnormality on EMG recordings with continuous motor unit activity of the paraspinal axial muscles is typically observed. Variants include "stiff-limb syndrome" producing focal stiffness typically affecting distal legs and feet.

Gait disorders refer to an abnormality in the manner or style of walking, which results from neuromuscular, arthritic, or other body changes. Gait is classified according to the system responsible for abnormal locomotion, and include hemiplegic gait, diplegic gait, neuropathic gait, myopathic gait, parkinsonian gait, choreiform gait, ataxic gait, and sensory gait.

Anesthesia/Sedation

Anesthesia is a pharmacologically induced and reversible state of amnesia, analgesia, loss of responsiveness, loss of skeletal muscle reflexes, decreased stress response, or all of these simultaneously. These effects can be obtained from a single drug which alone provides the correct combination of effects, or occasionally with a combination of drugs (e.g., hypnotics, sedatives, paralytics, analgesics) to achieve very specific combinations of results. Anesthesia allows patients to undergo surgery and other procedures without the distress and pain they would otherwise experience.

Sedation is the reduction of irritability or agitation by administration of a pharmacological agent, generally to facilitate a medical procedure or diagnostic procedure.

Sedation and analgesia include a continuum of states of consciousness ranging from minimal sedation (anxiolysis) to general anesthesia.

Minimal sedation is also known as anxiolysis. Minimal sedation is a drug-induced state during which the patient responds normally to verbal commands. Cognitive function and coordination may be impaired. Ventilatory and cardiovascular functions are typically unaffected.

Moderate sedation/analgesia (conscious sedation) is a drug-induced depression of consciousness during which the patient responds purposefully to verbal command, either alone or accompanied by light tactile stimulation. No interventions are usually necessary to maintain a patent airway. Spontaneous ventilation is typically adequate. Cardiovascular function is usually maintained.

Deep sedation/analgesia is a drug-induced depression of consciousness during which the patient cannot be easily aroused, but responds purposefully (not a reflex withdrawal from a painful stimulus) following repeated or painful stimulation. Independent ventilatory function may be impaired and the patient may require assistance to maintain a patent airway. Spontaneous ventilation may be inadequate. Cardiovascular function is usually maintained.

General anesthesia is a drug-induced loss of consciousness during which the patient is not arousable, even to painful stimuli. The ability to maintain independent ventilatory function is often impaired and assistance is often required to maintain a patent airway. Positive pressure ventilation may be required due to depressed spontaneous ventilation or drug-induced depression of neuromuscular function. Cardiovascular function may be impaired.

Sedation in the intensive care unit (ICU) allows the depression of patients' awareness of the environment and reduction of their response to external stimulation. It can play a role in the care of the critically ill patient, and encompasses a wide spectrum of symptom control that will vary between patients, and among individuals throughout the course of their illnesses. Heavy sedation in critical care has been used to facilitate endotracheal tube tolerance and ventilator synchronization, often with neuromuscular blocking agents.

In some embodiments, sedation (e.g., long-term sedation, continuous sedation) is induced and maintained in the ICU for a prolonged period of time (e.g., 1 day, 2 days, 3 days, 5 days, 1 week, 2 week, 3 weeks, 1 month, 2 months). Long-term sedation agents may have long duration of action. Sedation agents in the ICU may have short elimination half-life.

Procedural sedation and analgesia, also referred to as conscious sedation, is a technique of administering sedatives or dissociative agents with or without analgesics to induce a state that allows a subject to tolerate unpleasant procedures while maintaining cardiorespiratory function.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, Protecting Groups in Organic Synthesis, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative oxysterols that have been listed herein. The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK® AD-10, CHIRALCEL® OB, CHIRAL- CEL® OB-H, CHIRALCEL® OD, CHIRALCEL® OD-H, CHIRALCEL® OF, CHIRALCEL® OG, CHIRALCEL® OJ and CHIRALCEL® OK.

1H-NMR reported herein (e.g., for the region between δ (ppm) of about 0.5 to about 4 ppm) will be understood to be an exemplary interpretation of the NMR spectrum (e.g., exemplary peak integratations) of a compound.

Exemplary general method for preparative HPLC: Column: Waters RBridge prep 10 μm C18, 19*250 mm. Mobile phase: acetonitrile, water (NH4HCO3) (30 L water, 24 g NH4HCO3, 30 mL NH3·H2O). Flow rate: 25 mL/min.

Exemplary general method for analytical HPLC: Mobile phase: A: water (10 mM NH4HCO3), B: acetonitrile Gradient: 5%-95% B in 1.6 or 2 min Flow rate: 1.8 or 2 mL/min; Column: XBridge C18, 4.6*50 mm, 3.5 μm at 45 C.

LC-ELSD/MS Mobile Phase: 1.5 mL/4 L TFA in water (solvent A) and 0.75 mL/4 L TFA in acetonitrile (solvent B), using the elution gradient 30%-90% (solvent B) over 0.9 minutes and holding at 90% for 0.6 minutes at a flow rate of 1.2 mL/min; Column: Xtimate C18 2.1*30 mm, 3 μm; Column temperature: 50° C.; PDA Wavelength: UV 220 nm; MS ionization: ESI & ELSD.

Exemplary general method for SFC: Column: CHIRAL-PAK® AD CSP (250 mm*30 mm, 10 μm), Gradient: 45% B, A=NH3H2O, B=MeOH, flow rate: 60 mL/min. For example, AD_3_EtOH_DEA_5_40_25 ML would indicate: "Column: Chiralpak AD-3 150×4.6 mm I.D., 3 um Mobile phase: A: CO2 B:ethanol (0.05% DEA) Gradient: from 5% to 40% of B in 5 min and hold 40% for 2.5 min, then 5% of B for 2.5 min Flow rate: 2.5 mL/min Column temp: 35° C.".

HRMS Instrument: Agilent G230B LCMS-TOF The mobile phase: 0.1% FA in water (solvent A) and ACN (solvent B); Elution Gradient: 5%-95% (solvent B) over 3 minutes and holding at 95% for 1 minute at a flow rate of 1 mL/minute; Column: Xbridge Shield RP 18 5 μm, 2.1*50 mm; Ion Source: MS ESI source; Ion Mode: Positive; Nebulization Gas: Nitrogen; Drying Gas (N2) Flow: 8 L/min; Nebulizer Pressure: 35 psig; Gas Temperature: 325° C.; Sheath gas Temperature: 350° C.; Sheath gas flow: 11 L/min; Capillary Voltage: 3.5 KV; Fragmentor Voltage: 175 V.

Abbreviations: PE: petroleum ether; TLC: thin layer chromatography; petroleum ether; EtOAc: ethyl acetate; THF: tetrahydrofuran; PCC: pyridinium chlorochromate; t-BuOK: potassium tert-butoxide; 9-BBN: 9-borabicyclo [3.3.1]nonane; Pd(t-Bu3P)2: bis(tri-tert-butylphosphine) palladium(0); AcCl: acetyl chloride; i-PrMgCl: Isopropyl-magnesium chloride; TBSCl: tert-Butyl(chloro) dimethylsilane; (i-PrO)4Ti: titanium tetraisopropoxide; BHT: 2,6-di-t-butyl-4-methylphenoxide; Me: methyl; i-Pr: iso-propyl; t-Bu: tert-butyl; Ph: phenyl; Et: ethyl; Bz: benzoyl; BzCl: benzoyl chloride; CsF: cesium fluoride; DCC: dicyclohexylcarbodiimide; DCM: dichloromethane; DMAP: 4-dimethylaminopyridine; DMP: Dess-Martin periodinane; EtMgBr: ethylmagnesium bromide; TEA: triethylamine; AlaOH: alanine; Boc: t-butoxycarbonyl. Py: pyridine; TBAF: tetra-n-butylammonium fluoride; THF: tetrahydrofuran; TBS: t-butyldimethylsilyl; TMS: trimethylsilyl; TMSCF3: (Trifluoromethyl)trimethylsilane; Ts: p-toluenesulfonyl; Bu: butyl; Ti(OiPr)4: tetraisopropoxytitanium; LAH: Lithium Aluminium Hydride; LDA: lithium diisopropylamide; LiOH·H2O: lithium hydroxide hydrates; MAD: methyl aluminum bis(2,6-di-t-butyl-4-methylphenoxide); NBS: N-bromosuccinimide; Na2SO4: sodium sulfate; Na2S2O3: sodium thiosulfate; MeCN: acetonitrile; MeOH: methanol; Boc: t-butoxycarbonyl; MTBE: methyl tert-butyl ether; K-selectride: Potassium tri(s-butyl)borohydride.

Example 1: Synthesis of 1-(2-((3R,5R,8R,9R,10S, 13S,14S,17S)-3-hydroxy-13-methyl-3-(methyl-d3) hexadecahydro-1H-cyclopenta[a]phenanthren-17-yl)-2-oxoethyl)-1H-pyrazole-4-carbonitrite (Compound 1)

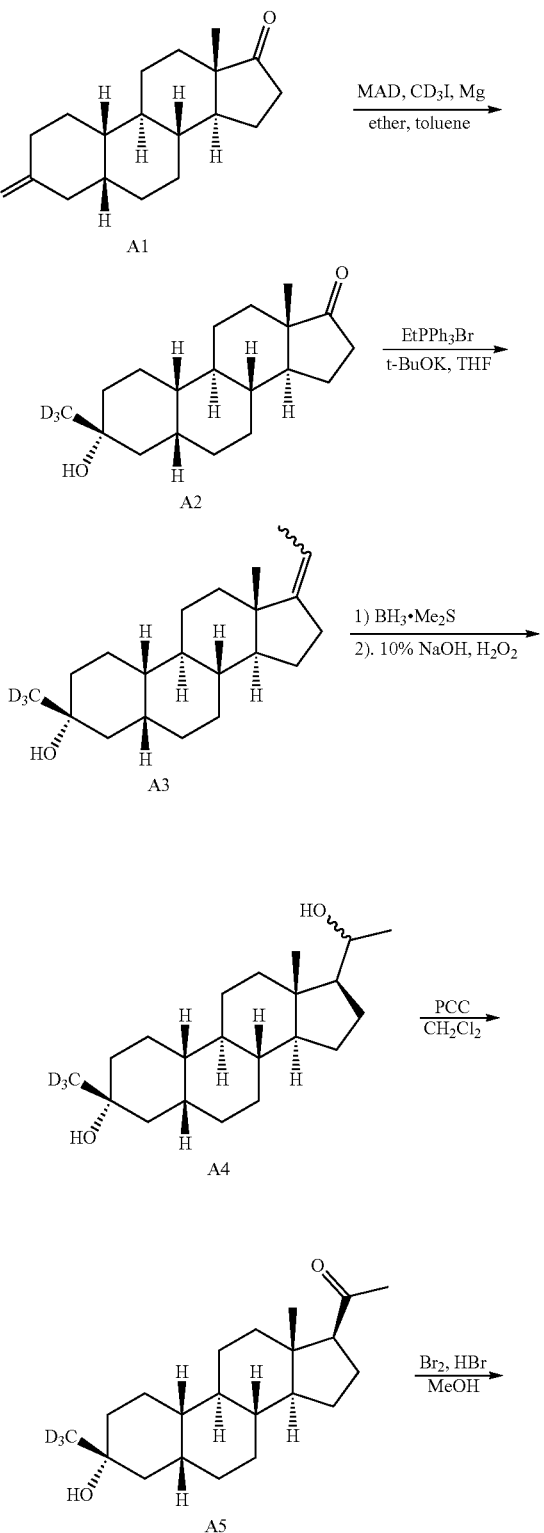

-continued

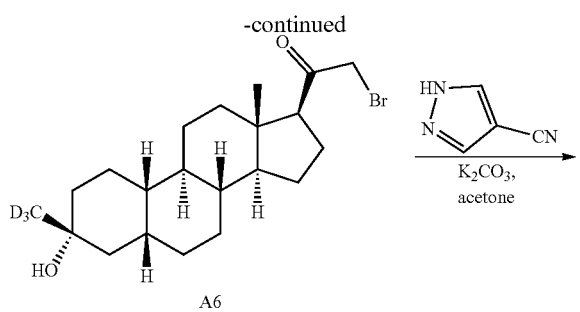

A6

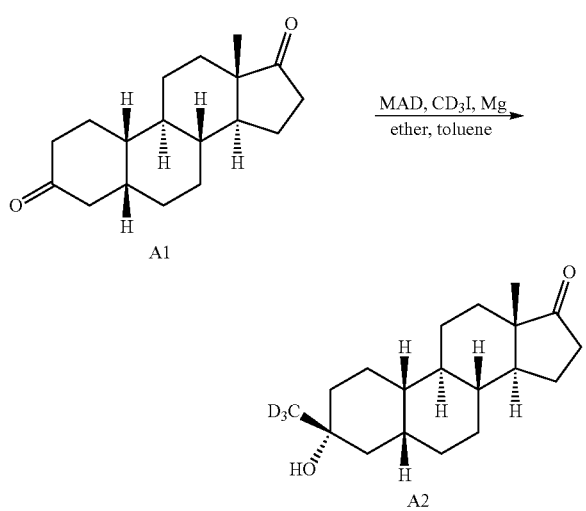

Synthesis of A2 filtered. The filter cake was washed EtOAc (200 mL), and the filtrate was combined. The organic layer was dried over $Na_2SO_4$, concentrated under vacuum, purified by column chromatography on silica gel (eluted with PE:EtOAc=10:1 to 2:1) to give A2 (1.1 g, 39%) as a solid.

$^1$H NMR (400 MHz, CDCl$_3$) δ$_H$ 2.49-2.35 (m, 1H), 2.14-1.98 (m, 1H), 1.95-1.70 (m, 7H), 1.70-1.00 (m, 15H), 0.86 (s, 3H).

Synthesis of A3

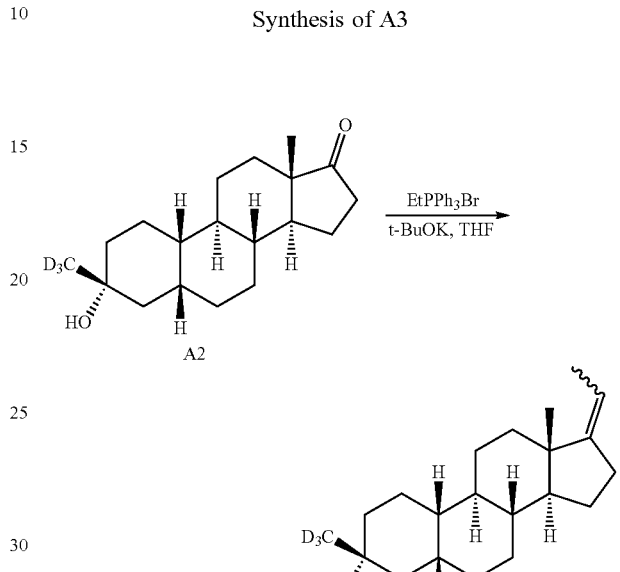

To a solution of EtPPh$_3$Br (6.33 g, 17.05 mmol) in 10 mL THF was added a solution of t-BuOK (1.91 g, 17.05 mmol) in THF (15 mL). The reaction mixture was stirred at 60° C. for 1 h, then to the mixture was added a solution of A2 (1 g, 3.41 mmol) in THF (10 mL), and the mixture was stirred at 60° C. for an additional 15 h. When TLC showed the staring material was consumed, and the reaction mixture was quenched with water (10 mL) and extracted with 150 mL of EtOAc. The combined organic layer was washed with brine, dried over Na$_2$SO$_4$ and concentrated to give crude product. The residue was purified by column chromatography on silica gel (eluted with PE:EtOAc=200:1-10:1) to give A3 (1 g, 95.89%) as a solid.

$^1$H NMR (400 MHz, CDCl$_3$) δ$_H$ 5.14-5.08 (m, 1H), 2.38-2.30 (m, 1H), 2.25-2.21 (m, 2H), 1.81-1.64 (m, 10H), 1.40-1.07 (m, 14H), 0.87 (s, 3H).

To a suspension of Mg (660 mg, 27.3 mmol) in ether (10 mL) was added solution of CD$_3$I (4 g, 27.3 mmol) in anhydrous ether (2.5 mL) dropwise under N$_2$ at 25° C. and inner temperature was raised to 35° C. The mixture was then stirred at 25° C. for 3 hours to give CD$_3$MgI, which can be used directly.

To a solution of 2,6-di-tert-butyl-4-methylphenol (12 g, 54.6 mmol) in toluene (20 mL) was added AlMe$_3$ (13.7 mL, 2 M in toluene, 27.3 mmol) dropwise at 10° C. The mixture was then stirred at 25° C. for 1 hour. To the mixture was added a suspension of A1 (2.5 g, 9.1 mmol) (described in U.S. Pat. No. 9,512,165) in toluene (7.5 mL) dropwise at −70° C. by dropwise under N$_2$. The mixture was stirred at −70° C. for 1 hour, then the solution of CD$_3$MgI in ether was added dropwise at −70° C. over 15 min. After the addition, the mixture was stirred at −70° C. for another 3 hours, before it was quenched by the addition of sat. aq. NH$_4$Cl (100 mL) at −70° C. The mixture was then warmed to 25° C. and Synthesis of A4

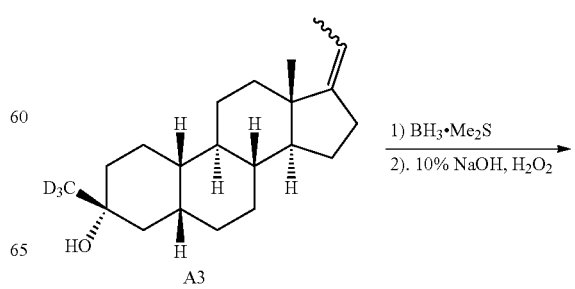

Synthesis of A6

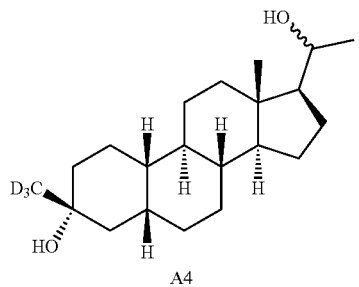

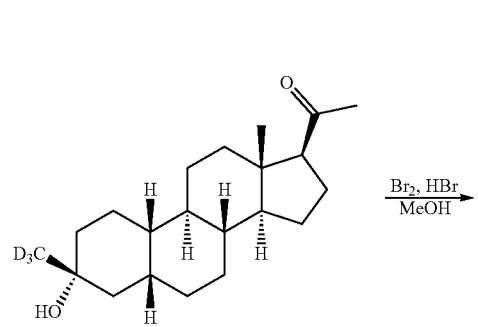

To a solution of A3 (1 g, 3.72 mmol) in dry THF (10 mL) was added BH$_3$·Me$_2$S (3.27 mL, 10 eq.) at 0° C. After stirring at 20° C. for 2 hours, the reaction mixture was cooled in an ice bath and quenched slowly by the addition of 3M aqueous NaOH (30 mL) followed by 30% aqueous solution of H$_2$O$_2$ (20 mL). After stirring at 20° C. for 1 h, the mixture was filtered, and the filtrate was extracted with EtOAc (50 mL*2). The combined organic layers was washed with aq. Na$_2$S$_2$O$_3$ (30 mL), dried over Na$_2$SO$_4$ and concentrated to afford A4 (1.2 g, crude). The crude product was used in the next step without further purification.

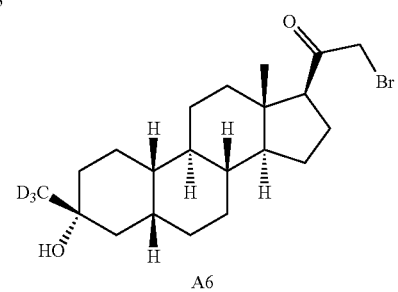

To a solution of A5 (0.8 g, 2.49 mmol) in 50 mL MeOH, was added HBr (3 drops) and Br$_2$ (0.14 mL, 2.74 mmol) at 25° C. The reaction was stirred at 25° C. for 1.5 h. When TLC showed the starting material consumed, the reaction mixture was quenched by the addition of aq·NaHCO$_3$ (30 mL) and concentrated. The mixture was extracted with 500 mL EtOAc, washed with brine (100 mL), dried over Na$_2$SO$_4$ and concentrated to afford A6 (1 g, Crude) as a solid.

$^1$H NMR (400 MHz, CDCl$_3$) δ$_H$ 3.92-3.91 (m, 2H), 2.85-2.75 (m, 1H), 2.20-2.10 (m, 1H), 1.93-1.71 (m, 11H), 1.44-1.09 (m, 12H), 0.63 (s, 3H).

Synthesis of A5

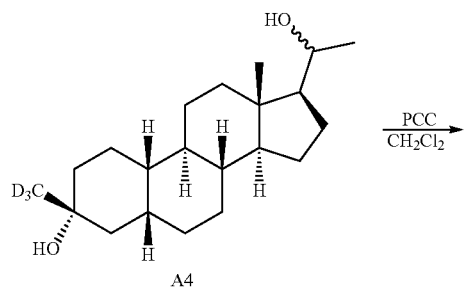

Synthesis of Compound 1

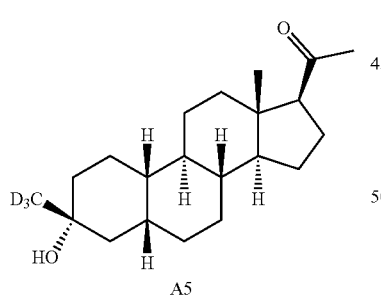

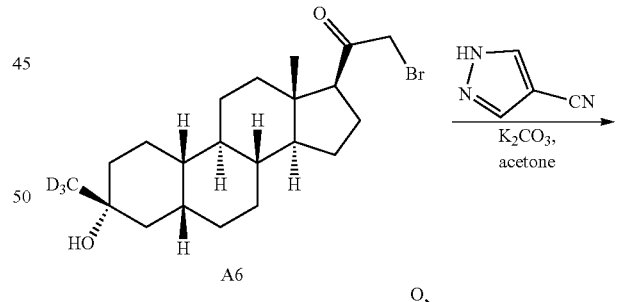

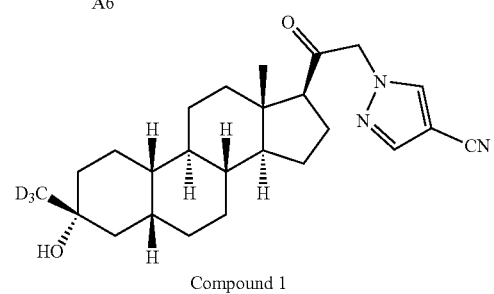

To a solution of A4 (1.2 g, Crude) in 15 mL CH$_2$Cl$_2$ was added silica gel (1.1 g) and PCC (0.96 g, 4.46 mmol) at 20° C., the reaction was stirred at 20° C. for 2 h. After TLC showed the starting material consumed, the mixture was filtered and concentrated. The residue was purified by column chromatograph on silica gel (eluted with PE:EtOAc=20:1-15:1-10:1-8:1-6:1) to give A5 (0.8 g, 83.6%) as a solid.

$^1$H NMR (400 MHz, CDCl$_3$) δ$_H$ 2.56-2.51 (m, 1H), 2.14-2.11 (m, 4H), 2.05-1.95 (m, 1H), 1.81-1.64 (m, 7H), 1.44-1.05 (m, 15H), 0.61 (s, 3H).

To a solution of A6 (0.15 g, 0.37 mmol) in 10 mL acetone was added K$_2$CO$_3$ (0.15 g, 1.11 mmol, 3 eq.) and 1H-pyrazole-4-carbonitrile (50 mg, 0.55 mmol, 1.5 eq). The reaction mixture was stirred at 23° C. for 2 hs. After TLC showed the starting material was consumed completed, the reaction was filtered with CH₂Cl₂ (20 mL) and concentrated. The residue was purified by column chromatography on silica gel (PE: EtOAc=10:1-8:1-6:1-5:1-4:1-2:1) to afford Compound 1 (54 mg, 35.14% yield) as a solid.

¹H NMR (400 MHz, CDCl₃) $\delta_H$ 7.86-7.81 (m, 2H), 5.04-4.88 (m, 2H), 2.61-2.59 (m, 1H), 2.25-2.15 (m, 1H), 2.06-2.03 (m, 1H), 1.81-1.74 (m, 6H), 1.49-1.27 (m, 12H), 1.11-1.09 (m, 3H), 0.67 (s, 3H). MS ESI calcd. for C25H32D3N3O2 [M+H]+ 412.58, found 395.

Example 2: Synthesis of 1-(2-((3R,5R,8R,9R,10S, 13S,14S,17S)-3-hydroxy-3,13-dimethylhexadeca-hydro-1H-cyclopenta[a]phenanthren-17-yl-17-d)-2-oxoethyl)-1H-pyrazole-4-carbonitrile (A10)

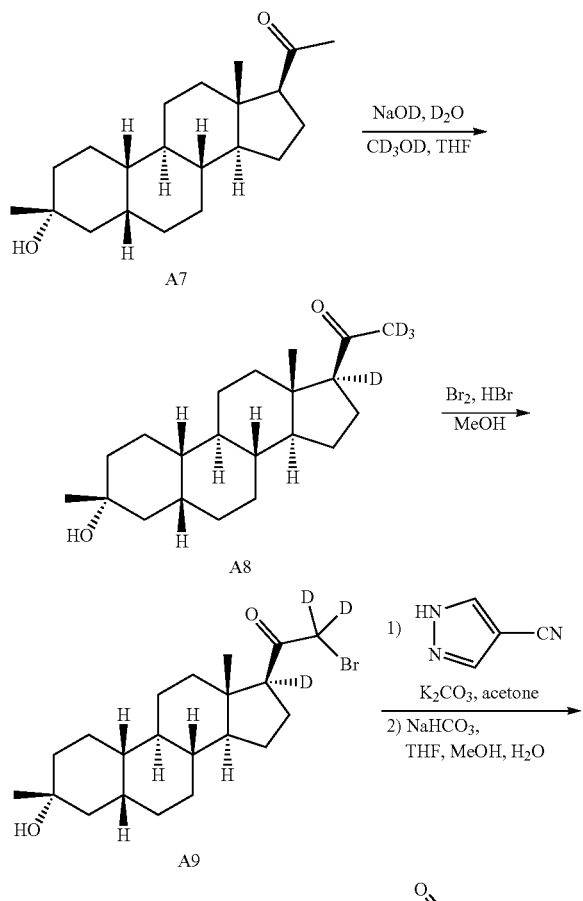

Synthesis of A8

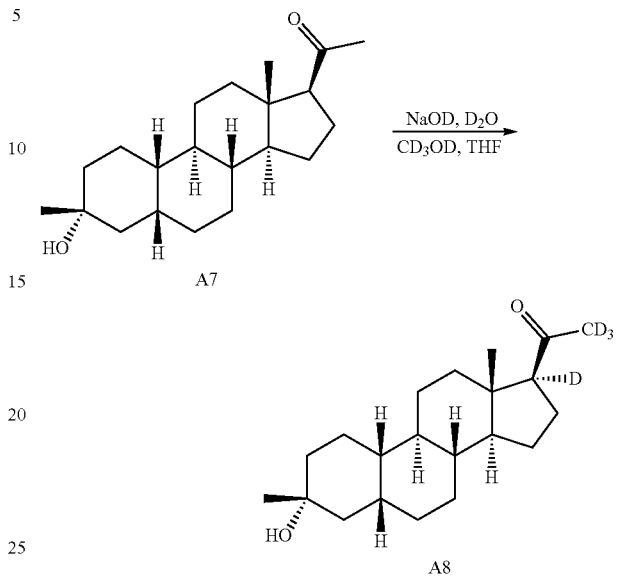

To a solution of A7 (1 g, 3.1 mmol, reported in patent 'WO2014/169833, 2014, A1') in THF (20 mL) was added D₂O (10 mL), CD₃OD (5 mL) and NaOD (96.2 mg, 40% in D₂O, 0.94 mmol). The mixture was stirred at 60° C. for 16 h. The reaction mixture was adjusted to pH=7 with AcOD (0.1 M in D₂O) after cooling. To the mixture was added NaCl (3 g) and PE (20 mL). The mixture was stirred for 5 min and the organic layer was separated, dried over Na₂SO₄, filtered and concentrated in vacuum to give an oil. As analysis indicated in complete deuteration, the reaction conditions were repeated. To a solution of the previous oil in THF (20 mL) was added D₂O (10 mL), CD₃OD (5 mL) and NaOD (96.2 mg, 40% in D₂O, 0.94 mmol). The mixture was stirred at 60° C. for 16 h. The reaction mixture was adjusted to pH=7 with AcOD (0.1 M in D₂O) after cooling. To the mixture was added NaCl (3 g) and PE (20 mL). The mixture was stirred for 5 min and the organic layer was separated, dried over Na₂SO₄, filtered, concentrated in vacuum to give A8 (900 mg, 90%) as an oil.

¹H NMR (400 MHz, CD₃OD) $\delta_H$ 2.25-1.95 (m, 3H), 1.85-1.55 (m, 10H), 1.50-0.80 (m, 14H), 0.60 (s, 3H).

Synthesis of A9

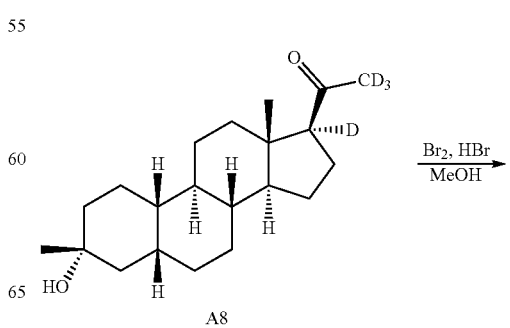

-continued

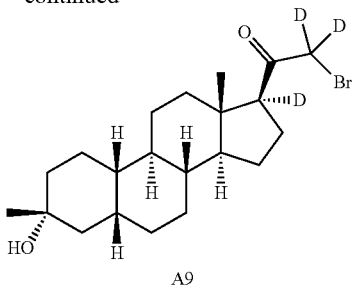

A9

To a solution of A8 (0.3 g, 0.93 mmol) in MeOH (3 mL) was added HBr (37.5 mg, 40%, 0.18 mmol) and Br$_2$ (148 mg, 0.93 mmol). The mixture was stirred at 15° C. for 3 h. The mixture was quenched by NaHCO$_3$ (20 mL, sat.) and extracted with EtOAc (20 mL). The organic layer was separated, dried over Na$_2$SO$_4$, filtered, concentrated in vacuum to give A9 (0.35 g, 94%) as an oil.

$^1$H NMR (400 MHz, CD$_3$OD) δ$_H$ 2.25-2.10 (m, 1H), 1.85-1.55 (m, 11H), 1.50-0.80 (m, 15H), 0.63 (s, 3H).

Synthesis of A10

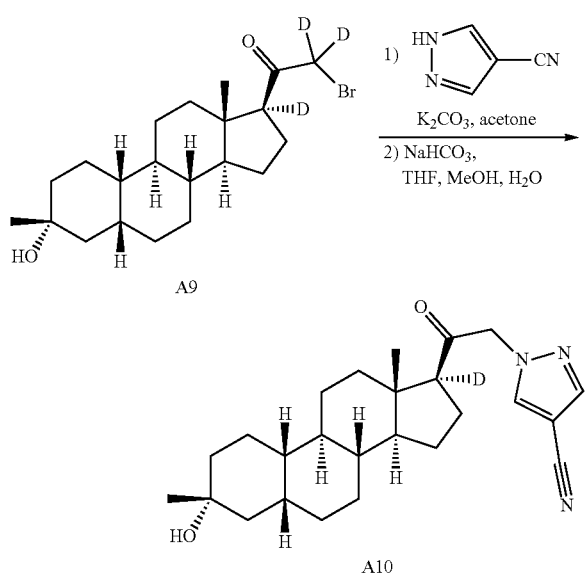

To a solution of A9 (0.35 g, 0.87 mmol) in acetone (3 mL) was added 4-cyano-pyrazole (323 mg, 3.5 mmol) and K$_2$CO$_3$ (487 mg, 3.5 mmol). The mixture was stirred at 15° C. for 1 h. The mixture was quenched by NH$_4$Cl (20 mL, sat.) and extracted with EtOAc (20 mL). The organic layer was separated, dried over Na$_2$SO$_4$, filtered, concentrated in vacuum and purified by flash column (20~60% EtOAc in PE) to give A10 (0.23 g, 64%, 12% 21-D was remained) as a solid.

To a solution of A10 (0.23 g, 12% 21-D remained, 0.56 mmol) in THF (5 mL) was added MeOH (10 mL) and NaHCO$_3$ (47 mg, 0.56 mmol) in water (5 mL). The mixture was stirred at 20° C. for 16 h. The mixture was diluted with EtOAc (50 mL) and washed with water (2×50 mL), dried over Na$_2$SO$_4$, filtered, concentrated in vacuum and triturated in hexane (30 mL) at 60° C. to give A10 (162 mg, 70%, D-ratio: 97.89%) as a solid.

$^1$H NMR (400 MHz, CDCl$_3$) δ$_H$ 7.86 (s, 1H), 7.81 (s, 1H), 5.10-4.80 (m, 2H), 2.25-2.15 (m, 1H), 2.10-2.00 (m, 1H), 1.90-1.65 (m, 7H), 1.45-1.30 (m, 9H), 1.30-1.20 (m, 6H), 1.30-1.00 (m, 3H), 0.67 (s, 3H); LC-ELSD/MS purity 100%, MS ESI calcd. for C25H35DN3O2 [M+H]+ 411, found 411; HRMS calcd. for C25H35DN3O2 [M+H]+ 411.2865, found 411.2815.

Example 3. Biological Data

Steroid Inhibition of TBPS Binding

[35S]-t-Butylbicyclophosphorothionate (TBPS) binding assays using rat brain cortical membranes in the presence of 5 mM GABA has been described (Gee et al, J. Pharmacol. Exp. Ther. 1987, 241, 346-353; Hawkinson et al, Mol. Pharmacol. 1994, 46, 977-985; Lewin, A. H et al., Mol. Pharmacol. 1989, 35, 189-194).

Briefly, cortices are rapidly removed following decapitation of carbon dioxide-anesthetized Sprague-Dawley rats (200-250 g). The cortices are homogenized in 10 volumes of ice-cold 0.32 M sucrose using a glass/teflon homogenizer and centrifuged at 1500×g for 10 min at 4° C. The resultant supernatants are centrifuged at 10,000×g for 20 min at 4° C. to obtain the P2 pellets. The P2 pellets are resuspended in 200 mM NaCl/50 mM Na—K phosphate pH 7.4 buffer and centrifuged at 10,000×g for 10 min at 4° C. This washing procedure is repeated twice and the pellets are resuspended in 10 volumes of buffer. Aliquots (100 mL) of the membrane suspensions are incubated with 3 nM [35S]-TBPS and 5 mL aliquots of test drug dissolved in dimethyl sulfoxide (DMSO) (final 0.5%) in the presence of 5 mM GABA. The incubation is brought to a final volume of 1.0 mL with buffer. Nonspecific binding is determined in the presence of 2 mM unlabeled TBPS and ranged from 15 to 25%. Following a 90 min incubation at room temp, the assays are terminated by filtration through glass fiber filters (Schleicher and Schuell No. 32) using a cell harvester (Brandel) and rinsed three times with ice-cold buffer. Filter bound radioactivity is measured by liquid scintillation spectrometry. Non-linear curve fitting of the overall data for each drug averaged for each concentration is done using Prism (GraphPad). The data are fit to a partial instead of a full inhibition model if the sum of squares is significantly lower by F-test. Similarly, the data are fit to a two component instead of a one component inhibition model if the sum of squares is significantly lower by F-test. The concentration of test compound producing 50% inhibition (IC50) of specific binding and the maximal extent of inhibition (Imax) are determined for the individual experiments with the same model used for the overall data and then the means+SEM.s of the individual experiments are calculated. Picrotoxin serves as the positive control for these studies as it has been demonstrated to robustly inhibit TBPS binding.

Various compounds are or can be screened to determine their potential as modulators of [35S]-TBPS binding in vitro. These assays are or can be performed in accordance with the above discussed procedures.

In Tables 2 below, A indicates a TBPS IC50 (μM)<0.01 μM, B indicates a TBPS IC50 (μM) of 0.01 μM to <0.1 μM, C indicates a TBPS IC50 (μM) of 0.1 μM to <1.0 μM, D indicates a TBPS IC50 (μM) of 1.0 μM to <10 μM, and E means≥10 μM.

TABLE 2

| Example | Compound ID | STRUCTURE | IC50 (µM) |
|---|---|---|---|
| 1 | Compound 1 | 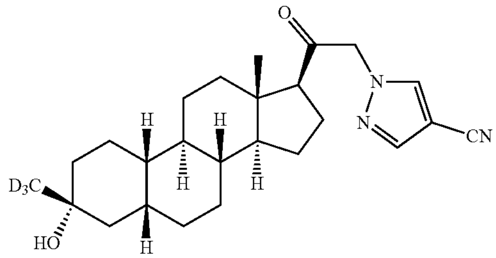 | A |
| 2 | A10 | 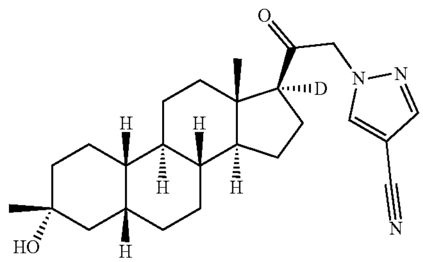 | A |

Example 4. Evaluation of Metabolic Stability of Compounds—Human CYP3A4 SUPERSOMEST™

SUPERSOMES™ Assay—To evaluate the metabolic stability of a compound described herein, e.g., a compound of Formula (I), one can take advantage of the following assay. The assay is only provided as an example and is a non-limiting method to evaluate the metabolic stability of the compounds described herein.

7.5 mM stock solutions of compounds described herein can be prepared in DMSO. The 7.5 mM stock solutions can be diluted to 50 mM in acetonitrile (ACN). Human CYP3A4 SUPERSOMES™ (1000 pmol/mL, purchased from BD Gentest.™. Products and Services) can be diluted to 62.5 pmol/mL in 0.1 M potassium phosphate buffer, pH 7.4, containing 3 mM MgCl2. The diluted supersomes can be added to wells of a 96-well polypropylene plate in triplicate. A 10 mL aliquot of the 50 mM test compound can be added to the SUPERSOMES™ and the mixture can be pre-warmed for 10 minutes. Reactions can be initiated by addition of pre-warmed NADPH solution. The final reaction volume can be 0.5 mL and can contain 50 pmol/mL CYP3A4 SUPERSOMES™, 1.0 mM test compound, and 2 mM NADPH in 0.1 M potassium phosphate buffer, pH 7.4, and 3 mM MgCl2. The reaction mixtures can be incubated at 37° C., and 50 mL aliquots can be removed at 0, 5, 10, 20, and 30 minutes and added to 96-well plates which can contain 50 mL of ice-cold ACN with internal standard to stop the reactions. The plates can be stored at 4° C. for 20 minutes after which 100 mL of water was added to the wells of the plate before centrifugation to pellet precipitated proteins. Supernatants were transferred to another 96-well plate and analyzed for amounts of parent remaining by LC-MS/MS using an Applied Bio-systems API 4000 mass spectrometer.

Data Analysis:

The in vitro half-lives (t.sub.½ values) for test compounds can be calculated from the slopes of the linear regression of LN(% parent remaining) vs incubation time relationship: in vitro t½=0.693/k, where k=−[slope of linear regression of % parent remaining(ln)vs incubation time].

Example 5. Evaluation of Pharmacokinetics in Rats for Compounds

To evaluate the pharmacokinetics of the compounds described herein, e.g., a compound of Formula (I), one can take advantage of the following assay. The assay is only provided as an example and is a non-limiting method to evaluate the pharmacokinetics of the compounds described herein.

The compounds described herein can be discrete dosed to rats via oral gavage (PO). Each compound can be administered at a dose of 10 mg/kg to three rats (N=3 rats/compound; total of 9 rats in the study). Each compound can formulated in 100% PEG400 at a concentration of 2 mg/mL. Blood samples can be collected from each rat at 15 and 30 minutes, and 1, 2, 4, 6, 8, 12, 24, 48, and 72 hours post-dose. Blood samples can be centrifuged to obtain plasma. Plasma samples can be analyzed for concentrations of the dosed compound at each time point using LC-MS/MS. The limit of quantitation of each compound was 1 ng/mL.

The rat t½ values can be determined by non-compartmental analysis using WinNonlin software.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

We claim:
1. A process for preparing Compound 1,

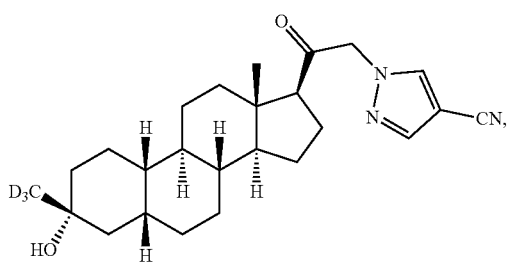

Compound 1 the process comprising:
reacting a compound of Formula A6:

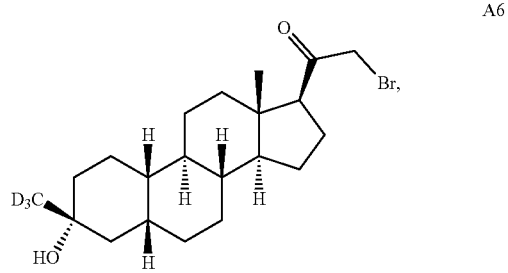

A6 with the compound represented by:

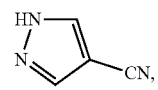

in the presence of a base and an organic solvent to provide Compound 1.

2. The process of claim 1, wherein the base is potassium carbonate and the organic solvent is acetone.

3. The process of claim 1, further comprising preparing the compound of Formula A6:

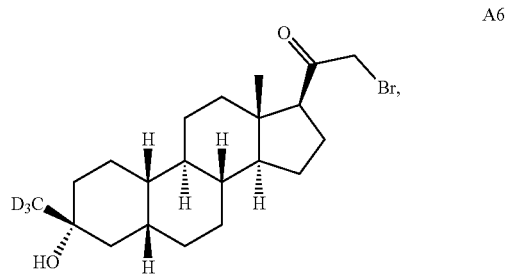

A6 by reacting a compound of Formula A5:

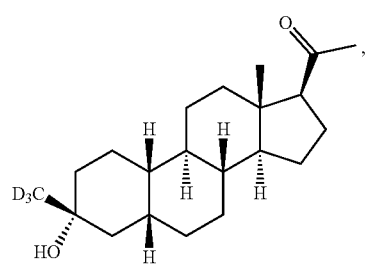

A5 with Br$_2$ in the presence of an acid to provide the compound of Formula A6.

4. The process of claim 3, wherein the acid comprises hydrogen bromide.

5. The process of claim 3, further comprising preparing the compound of Formula A5:

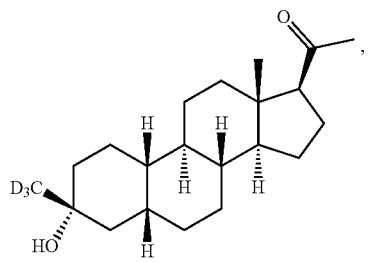

by reacting a compound of Formula A4:

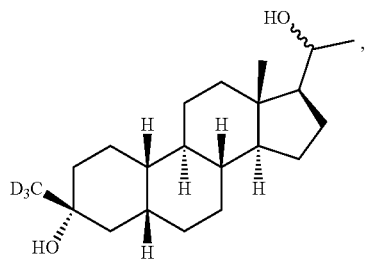

with an alcohol oxidizing agent in the presence of a solvent to provide the compound of Formula A5.

6. The process of claim 5, wherein the alcohol oxidizing agent is pyridinium chlorochromate, and the solvent is dichloromethane.

7. The process of claim 5, further comprising preparing the compound of Formula A4:

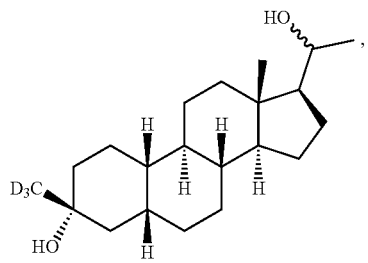

by reacting a compound of Formula A3:

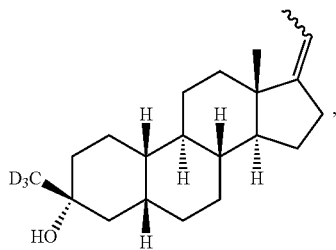

with: a) a borane reagent; and followed by b) a hydroxide base and an oxidizing agent; in the presence of a solvent to provide the compound of Formula A4.

8. The process of claim 7, wherein the borane reagent is borane dimethylsulfide, the hydroxide base is sodium hydroxide, the oxidizing agent is hydrogen peroxide, and the solvent is tetrahydrofuran or water.

9. The process of claim 7, further comprising preparing the compound of Formula A3:

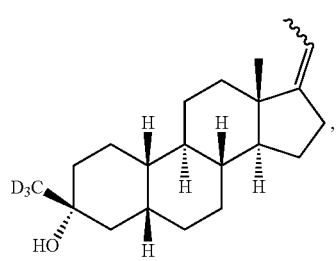

by reacting a compound of Formula A2:

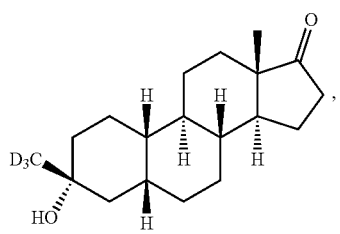

with EtPPh$_3$Br in the presence of a base and a solvent to provide the compound of Formula A3.

10. The process of claim 9, wherein the base is potassium tert-butoxide and the solvent is tetrahydrofuran.

* * * * *